US007964767B2

(12) United States Patent
Kodama et al.

(10) Patent No.: US 7,964,767 B2
(45) Date of Patent: Jun. 21, 2011

(54) TRANSGENIC MICE EXPRESSING BACULOVIRUS SOLUBLE GP64 AND METHODS OF USING SUCH MICE TO MAKE ANTIBODIES

(75) Inventors: Tatsuhiko Kodama, Tokyo (JP); Yoshiki Yamada, Tokyo (JP); Nobuo Kamada, Shizuoka (JP); Kou-Ichi Jishage, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/594,690

(22) PCT Filed: Mar. 31, 2005

(86) PCT No.: PCT/JP2005/006298
§ 371 (c)(1),
(2), (4) Date: Jun. 26, 2007

(87) PCT Pub. No.: WO2005/094572
PCT Pub. Date: Oct. 13, 2005

(65) Prior Publication Data
US 2008/0040820 A1    Feb. 14, 2008

(30) Foreign Application Priority Data
Mar. 31, 2004    (JP) .................................. 2004-107669

(51) Int. Cl.
*A01K 67/027*    (2006.01)
*C12P 21/00*    (2006.01)
(52) U.S. Cl. ............................................. 800/18; 800/6
(58) Field of Classification Search .................... 800/18, 800/3, 6
See application file for complete search history.

(56) References Cited

U.S. PATENT DOCUMENTS

| 5,500,346 | A | 3/1996 | Bright et al. |
| 5,849,525 | A | 12/1998 | Hediger |
| 6,270,978 | B1 | 8/2001 | Bright et al. |
| 6,713,278 | B1 | 3/2004 | Bouvier et al. |
| 2005/0004227 | A1 | 1/2005 | Saitoh |
| 2005/0222391 | A1 | 10/2005 | Kodama et al. |
| 2005/0281825 | A1 | 12/2005 | Kodama et al. |
| 2006/0084119 | A1 | 4/2006 | Saitoh et al. |
| 2006/0210569 | A1 | 9/2006 | Kodama et al. |

FOREIGN PATENT DOCUMENTS

| AU | 9676557 | 6/1997 |
| EP | 1142473 | 10/2001 |
| EP | 1 514 928 | 3/2005 |
| EP | 1 731 032 | 12/2006 |
| JP | 6-261761 | 9/1994 |
| JP | 8-134100 | 5/1996 |
| JP | 11-000172 | 1/1999 |
| JP | 2001-197846 | 7/2001 |
| JP | 2001-139496 | 5/2005 |
| KR | 1999-0071666 | 9/1999 |
| WO | WO 97/19919 | 6/1997 |
| WO | WO 98/46777 | 10/1998 |
| WO | WO 00/28016 | 5/2000 |
| WO | WO 03/033024 A1 | 4/2003 |
| WO | WO 03/047621 A1 | 6/2003 |
| WO | WO 03/083116 A1 | 10/2003 |
| WO | WO 03/104453 A1 | 12/2003 |

OTHER PUBLICATIONS

Saitoh (J. Immunological Methods, 2007, vol. 332, p. 104-117).*
Tsuchiya (Jan. 21, 2003, therapeutic antibody presentation, p. 1-21).*
Mancini (1993, J. Med. Virol., vol. 39, p. 67-74).*
D'Onofrie, "Making the case for acncer prevention in the schools", Journal of School Health 59(5):225-227, 1989.
Inoue et al., "Regulation of human peptide transporter 1 (PEPT1) in gastric cancer cells by anticancer drugs", Cancer Letters 230:72-80, 2005.
Pardee, "Tumor progression—targets for differential therapy", Journal of Cellular Physiology 209(3):589-591, 2006 (abstract only).
ATCC Web Catalog, "Tumor Cell Lines" www.atcc.org (2007), 15 pages.
Basu et al., "Screening of Anti-PepT1 Antibodies Using Indirect ELISA," *Pharmaceutical Research*, 13(9 Suppl.):S-37, Abstract No. APQ 1137 (1996).
Basu SK et al., "Development and Utility of Anti-PepT1 Anti-Peptide Polyclonal Antibodies", *Pharmaceutical Research*, 15(2):338-342 (1998).
Blissard et al., "Baculovirus gp64 Gene Expression: Analysis of Sequences Modulating Early Transcription and Transactivation by IE1," *J. Virol.*, 65:5820-5827 (1991).
Blissard et al., "Location, Sequence, Transcriptional Mapping, and Temporal Expression of the gp64 Envelope Glycoprotein Gene of the *Orgyia pseudotsugata* Multicapsid Nuclear Polyhedrosis Virus," *Virology*, 170:537-555 (1989).
Boublik et al., "Eukaryotic Virus Display: Engineering the major Surface Glycoprotein of the Autographa californica Nuclear Polyhedrosis Virus (ScNPV) for the Presentation of Foreign Proteins on the Virus Surface," *Biotechnology*, 13: 1079-1084 (1995).

(Continued)

*Primary Examiner* — Michael C. Wilson
(74) *Attorney, Agent, or Firm* — Fish & Richardson P.C.

(57) ABSTRACT

Membrane proteins that are background antigens were solubilized, and transgenic animals were produced using genes encoding these soluble proteins. Antibodies against the background antigen membrane proteins comprised in the immunogens were not found in these transgenic animals, and even when genes encoding soluble proteins were used, immunotolerance against the full-length membrane proteins could be induced. Moreover, by expressing the background antigen membrane proteins as soluble proteins inside the bodies of transgenic animals, unfavorable phenotypes that appear when the full-length membrane proteins are expressed could be avoided, and such animals were made widely available as immunized animals.

14 Claims, 4 Drawing Sheets

OTHER PUBLICATIONS

"Cancer Classification," SEER Training Website, www.training.seer.cancer.gov/module_cancer_disease/unti3-categories2_by_histology (2005), 3 pages.

Friedman et al., "Characterization of the Intestinal Transport Parameters for Small Peptide Drugs," *J. Control. Release*, 13:141-146 (1990).

Friedman et al., "Passive and Carrier-Mediated Intestinal Absorption Components of Two Angiotensin Converting Enzyme (ACE) Inhibitor Prodrugs in Rats: Enalapril and Fosinopril," *Pharm. Res.*, 6:1043-1047 (1989).

Ganapathy et al., "Proton-coupled solute transport in the animal cell plasma membrane," *Curr. Opin. Cell Biol.*, 3:695-701 (1991).

Garcia et al., "cDNA Cloning of MCT2, a Second Monocarboxylate Transporter Expressed in Different Cells than MCT1," *The Journal of Biological Chemistry*, 270: 1843-1849 (1995).

Gonzalez et al., "An Oligopeptide Transporter is Expressed at High Levels in the Pancreatic Carcinoma Cell Lines AsPc-1 and Capan-2," *Cancer Res.*, 58(3): 519-525 (1998).

Grever et al., "The National Cancer Institute: Cancer Drug Discovery and Development Program," *Seminars in Oncology*, 19(6): 622-638 (1992).

Hefferon et al., "Host Cell receptor Binding by Baculovirus GP64 and Kinetics of Virion Entry," *Virology*, 258: 455-468 (1999).

Higgins, C.F., "ABC Transporters: From Microorganisms to Man," *Annu. Rev. Cell Biol.*, 8:67-113 (1992).

Houdebine, L.M., "Transgenic Animal Bioreactors," *Transgenic Res.*, 9: 305-320 (2000).

Hsu et al., "Overexpression of Human Intestinal Oligopeptide Transporter in Mammalian Cells via Adenoviral Transduction," *Pharm. Res.*, 15:1376-1381 (1998).

Kamada et al., "Generation of GP64-Expressing Mice and Induction of Tolerance to Budding Baculoviruses," *Nihon Bunshi Seibutsu Gakkai Nenkai Program Koen Yoshishu*, Abstract No. 1PC-162, p. 659 (2003) (Translation Provided).

Karaki et al., "Production of anti-HLA class I alloantibodies using HLA-B51 transgenic mice," *Nihonmenekigakkaisoukai Gakujutsushuukaikiroku*, Abstract No. C61, p. 197 (1990) (Translation Provided).

Knutter et al., "A Novel Inhibitor of the Mammalian Peptide Transporter PEPT1," *Biochemistry*, 40(14):4454-4488 (2001).

Kolb et al., "Insertion of a Foreign Gene into the β-Casein Locus by Cre-Mediated Site-Specific Recombination," *Gene*, 227: 21-31 (1999).

LaRiviere et al., "Transgenic Studies of Pain and Analgesia: Mutation of Background Genotype?" *The Journal of Pharmacology and Experimental Therapeutics*, 297: 467-473 (2001).

Lee et al., "Biopharmaceutics of transmucosal peptide and protein drug administration: role of transport mechanisms with a focus on the involvement of PepT1", *J. Control Release*, 62(1-2):129-140 (1999).

Leiter, E.H., "Mice with Targeted Gene Disruptions of Gene Insertions for Diabetes Research: Problems, Pitfalls, and Potential Solutions," *Diabetologia*, 45: 296-308 (2002).

Liang et al., "Human Intestinal $H^+$/Peptide Cotransporter. Cloning, Functional Expression, and Chromosomal Localization," *J. Biol. Chem.*, 270:6456-6463 (1995).

Lindley et al., "Production of Monoclonal Antibodies Using Recombinant Baculovirus Displaying GP64-Fusion Proteins," *Journal of Immunological Methods*, 234: 123-135 (2000).

Liu et al., "Molecular cloning of PEPT2, a new member of the H+/peptide cotransporter family, from human kidney," *Biochim. Biophys. Acta*, 1235:461-466 (1995).

Loisel et al., "Recovery of homogeneous and functional $α_2$-adrenergic receptors from extracellular baculovirus particles", *Nat Biotechnol*, 15(12):1300-1304 (1997).

Lu et al., "Characterization of a Truncated Soluble Form of the Baculovirus (AcMNPV) Major Envelope Protein Gp64," *Protein Expression and Purification*, 24: 196-201 (2002).

Mancini et al., "Induction of Anti-Hepatitis B Surface Antigen (HBsAg) Antibodies in HBsAg Producing Transgenic Mice: A Possible Way of Circumventing 'Nonresponse' to HBSAg," *Journal of Medical Virology*, 39: 67-74 (1993).

Mangor et al., "A GP64-Null Baculovirus Pseudotyped with Vesicular Stomatitis Virus G Protein", *Journal of Virology*, 75(6):2544-2556 (2001).

Mikhailov et al., "Expression of functionally active ATP-sensitive K-channels in insect cells using baculovirus", *FEBS Lett*, 429(3):390-394 (1998).

Miyasaka et al., "Characterization of Human Taurine Transported Expressed in Insect Cells Using a Recombinant Baculovirus," *Protein Expression and Purification*, 23: 389-397 (2001).

Monsma et al., "Identification of a Membrane Fusion Domain and an Oligomerization Domain in the Baculovirus GP64 Envelope Fusion Protein," *Journal of Virology*, 69: 2583-2595 (1995).

Monsma et al., "The GP64 Envelope Fusion Protein is an Essential Baculovirus Protein Required for Cell-to-Cell Transmission of Infection," *Journal of Virology*, 70: 4607-4616 (1996).

Mrsny RJ., "Oligopeptide Transporters as Putative Therapeutic Targets for Cancer Cells," *Pharm Res*. 15(6):816-818 (1998).

Muranushi et al., "Transport Characteristics of Ceftibuten, a New Oral Cephem, in Rat Intestinal Brush-Border Membrane Vesicles: Relationship to Oligopeptide and Amino β-Lactam Transport," *Pharm. Res.*, 6:308-312 (1989).

Murray, J.D., "Genetic Modification of Animals in the Next Century," *Theriogenology* 51: 149-159 (1999).

Nakanishi et al., "Cancer Cell-Targeted Drug Delivery Utilizing Oligopeptide Transport Activity," *Int. J. Cancer*, 88(2):274-280 (2000).

Nakashima et al., "Kinetics and Mechanism of in Vitro Uptake of Amino-β-Lactam Antibiotics by Rat Small Intestine and Relation to the Intact-Peptide Transport System," *Biochem. Pharmacol*, 33:3345-3352 (1984).

Nishimura et al., "Expression of the Human MHC, HLA-DQw6 Genes Alters the Immune Response in C57BL/6 Mice," *J. Immunol.*, 145:353-360 (1990).

Noe et al., "Characterization of the Mouse Bile Salt Export Pump Overexpressed in the Baculovirus System", *Hepatology*, 33(5):1223-1231 (2001).

Ogihara et al., "Immuno-Localization of $H^+$/Peptide Cotransporter in Rat Digestive Tract," *Biochem. Biophys. Res. Commun.*, 220:848-852 (1996).

Ohtomo et al., "Generation of Functional Antibodies Using GP64-Expressing/CCR2 Knock-Out Mice and CCR2-Expressing Baculoviruses," *Nihon Bunshi Seibutsu Gakkai Nenkai Program Koen Yoshishu*, Abstract No. 1PC-164, 26: 660 (2003) (Translation Provided).

Okamoto et al., "Generation of monoclonal antibodies directed against allotypic epitopes of HLA class II antigen by utilizing HLA-DQw6 transgenic mice," *Nihonmenekigakkaisoukai Gakujutsushuukaikiroku*, Abstract No. C62, p. 197 (1990) (Translation Provided).

Okano et al., "$H^+$ Coupled Uphill Transport of Aminocephalosporins via the Dipeptide Transport System in Rabbit Intestinal Brush-border Membranes," *J. Biol. Chem.*, 261:14130-14134 (1986).

Sai et al., "Selective Delivery of Peptide Anticancer Drugs via Oligopeptide Transporter Expressed in Cancer Cells," *Proceedings of the Millennium World Congress of Pharmaceutical Science*, p. 61, Abstract No. 2-2124 (Apr. 16-20, 2000).

Sai Y. et al., "Immunolocalization and pharmacological relevance of oligopeptide transporter PepT1 in intestinal absorption of α-lactam antibiotics", *FEBS Lett*, 392(1):25-29 (1996).

Saito et al., "Cloning and Characterization of a Rat $H^+$/Peptide Cotransporter Mediating Absorption of β-Lactam Antibiotics in the Intestine and Kidney," *J. Pharmacol. Exp. Ther.*, 275:1631-1637 (1995).

Saito et al., "Molecular cloning and tissue distribution of rat peptide transporter PEPT2," *Biochim. Biophys. Acta*, 1280:173-177 (1996).

Sakaguchi T. et al., "The Ion Channel Activity of the Influenza Virus $M_2$ Protein Affects Transport through the Golgi Apparatus", *J Cell Biol.*, 133(4):733-747 (1996).

Satoi et al., "Genetic Immunization of Wild-Type and Hepatitis C Virus Transgenic Mice Reveals a Hierarchy of Cellular Immune Response and Tolerance Induction against Hepatitis C Virus Structural Proteins," *J. Virol.*, 75:12121-12127 (2001).

Seliger et al., "Analysis of the MHC Class I Antigen Presentation Machinery in Human Embryonal CarcinomasL Evidence for Deficiencies in TAP, LMC, and MHC Class I Expression and Their Upregulation by IFN-γ," *Scandinavian Journal of Immunology*, 46: 625-632 (1997) (Abstract).

Shen et al., "Localization of PEPT1 and PEPT2 proton-coupled oligopeptide transporter mRNA and protein in rat kidney," *Am. J. Physiol.*, 276:F658-F665 (1999).

Sigmund, C.D., "Viewpoint: Are Studies in Genetically Altered Mice out of Control?" *Arterioscler. Thromb. Vasc. Biol.*, 20: 1425-1429 (2000).

Steiner et al., "The PTR family: a new group of peptide transporters," *Mol. Microbiol.*, 16:825-834 (1995).

Strehlow et al., "Retroviral membrane display of apoptotic effector molecules", *Proc. Natl. Acad. Sci. USA*, 97(8):4209-4214 (2000).

Sugano et al., "Quantitative Structure-Intestinal Permeability Relationship of Benzamidine Analogue Thrombin Inhibitor," *Bioorg Med. Chem. Lett*, 10(17):1939-1942 (2000).

Sun D. et al., "Drug Inhibition of Gly-Sar Uptake and hPepT1 Localization using hPepT1-GFP Fusion Protein", *AAPS PharmSci.*, 3(1):1-9 (2001).

Suzuki et al., "Effects of Retinoic Acid on Lung Smooth Muscle Cells," Meeting on Experimental Biology: Translating The Genome (Apr. 17-21, 2004) as published in FASEB Journal, 18(4-5): 355-356 (2004) (Abstract).

Szakács et al., "Characterization of the ATPase Cycle of Human ABCA1: Implications for Its Function as a Regulator Rather Than an Active Transporter", *Biochem Biophys Res Commun*, 288(5):1258-1264 (2001).

Takahashi et al., "Interaction of β-Lactam Antibiotics with $H^+$ Peptide Cotransporters in Rat Renal Brush-Border Membranes," *J. Pharmacol. Exp. Ther.*, 286:1037-1042 (1998).

Tamura et al., "CD14 Transgenic Mice Expressing Membrane and Soluble Forms: Comparisons of Levels of Cytokines and Lethalities in Response to Lipopolysaccharide Between Transgenic and Non-Transgenic Mice," *International Immunology*, 11:333-339 (1999).

Terada et al., "Characterization of Stably Transfected Kidney Epithelial Cell Line Expressing Rat $H^+$/Peptide Cotransporter PEPT1: Localization of PEPT1 and Transport of β-Lactam Antibiotics," *J. Pharmacol. Exp. Ther.*, 281:1415-1421 (1997).

Terada et al., Tanpakushitsu Kakusan Koso (Protein, nucleic acid and enzyme),46(5):621-628 (2001) (Translation Provided).

Tsuchiya, "Therapeutic Antibody," Presentation, Chugai Pharmaceutical Co., Ltd., 21 pages (Jan. 21, 2003).

Watanabe et al., "Enhanced Immune Responses in Transgenic Mice Expressing a Truncated Form of the Lymphocyte Semaphorin CD100," *J. Immunol.* 167: 4321-4328 (2001).

Zhou et al., "Characterization of an oligopeptide transporter in renal lysosomes", *Biochim Biophys Acta*, 1466(1-2): 372-378 (2000).

Braunagel et al., "*Autographa californica* Nuclear Polyhedrosis Virus, PDV, and ECV Viral Envelopes and Nucleocapsids: Structural Proteins, Antigens, Lipid and Fatty Acid Profiles," *Virology*, 202:315-320 (1994).

Grabherr et al., "Developments in the use of baculoviruses for the surface display of complex eukaryotic proteins," *Trends in Biotechnology*, 19:231-236 (2001).

Marheineke et al., "Lipid composition of Spodoptera frugiperda (Sf9) and Trichoplusia ni (Tn) insect cells used for baculovirus infection," *FEBS Letters*, 441:49-52 (1998).

Bachmann et al., "Correlation of Tolerogenicity of a Viral Antigen with Its Immunogenicity," *The Journal of Immunology*, 158:5106-5111 (1997).

Breyer et al., "Mutational analysis of ligand binding activity of $β_2$ adrenergic receptor expressed in *Escherichia coli*," *EMBO J.*, 9(9):2679-2684 (1990).

Campbell, "Monoclonal antibody technology", Elsevier Science Publishing Company, Inc., New York, pp. 1-33, 1984.

Clark, M., "Antibody humanization: a case of the 'Emperor's new clothes'?," *Immunol. Today*, 21(8):397-402 (2000).

Covitz et al., "Membrane Topology of the Human Dipeptide Transporter, hPEPT1, Determined by Epitope Insertions," *Biochemistry*, 37:15214-15221 (1998).

Kanamitsu, Kotai Kogaku Nyumon, 33-6 (1994) (English translation included).

Kawaguchi et al., "Gan Chiryo to Syukusyu: Frontiers in Cancer Treatment," 13(1):12-20 (2001).

McLaughlin, "Rituximab: perspective on single agent experience, and future directions in combination trials," *Critical Reviews in Oncology/Hematology*, 40:3-16 (2001).

Ramamoorthy et al., "Proton/peptide cotransporter (PEPT 2) from human kidney: Functional characterization and chromosomal localization," *Biochimica et Biophysica Acta*, 1240:1-4 (1995).

Renes et al., "ATP- and glutathione-dependent transport of chemotherapeutic drugs by the multidrug resistance protein MRP1," *Br. J. Pharmacol.*, 126:681-688 (1999).

Saitoh et al., "Recovery of functional peptide transporter PepT1 in budded baculovirus fraction," *Protein Expr. Purif.*, 46(1):130-135 (2006).

Steinhoff et al., "Variable Immune Response Against a Developmentally Regulated Self-Antigen," *Journal of Autoimmunity*, 12:27-34 (1999).

Tabas et al., "A high-throughput assay for measurement of multidrug resistance protein-mediated transport of leukotriene C4 into membrane vesicles," *Anal. Biochem.*, 310:61-66 (2002).

Tada et al., "Complement-dependent cytolysis," *Dictionary of Immunology $3^{rd}$ Edition*, 144 (1993).

Tate et al., "Molecular Chaperones Stimulate the Functional Expression of the Cocaine-Sensitive Serotonin Transporter," *J. Biol. Chem.*, 274(25):17551-17558 (1999).

Tsuruo et al., "Inhibition of Multidrug-resistant Human Tumor Growth in Athymic Mice by Anti-P-glycoprotein Monoclonal Antibodies," *Jpn. J Cancer Res.*, 80:627-631 (1989).

Vivekananda et al., "Monoclonal antibodies as tools in membrane biochemistry. Identification and partial characterization of the dicarboxylate transporter from pea leaf mitochondria," *J. Biol. Chem.*, 263(10):4782-4788 (1988).

Walker et al., "Substrate upregulation of the human small intestinal peptide transporter, hPepT1," *Journal of Physiology*, 507.3:697-706 (1998).

Yamada et al., "Preparation of anti-PepT1 monoclonal antibody using Viral display and gp64 transgenic mice," *Nihon Bunshi Seibutsu Gakkai Nenkai Program Koen Yoshishu*, 26:660(#1PC-163) (2003) (English translation included).

Fish & Richardson, P.C., Response to Restriction Requirement dated Jun. 6, 2007 in U.S. Appl. No. 10/492,376, filed Jul. 6, 2007, 1 page.

Fish & Richardson P.C., Amendment in Reply to Action dated Sep. 17, 2007 in U.S. Appl. No. 10/492,376, filed Jan. 17, 2008, 10 pages.

Fish & Richardson P.C., Response to Restriction Requirement dated Jun. 13, 2008 in U.S. Appl. No. 10/497,900, filed Jul. 11, 2008, 1 page.

Fish & Richardson P.C., Amendment in Reply to Action dated Sep. 19, 2007 in U.S. Appl. No. 10/497,900, filed Feb. 19, 2008, 9 pages.

Fish & Richardson P.C., Amendment in Reply to Action dated Oct. 30, 2008 in U.S. Appl. No. 10/497,900, filed Mar. 27, 2009, 8 pages.

USPTO Notice of Allowance in U.S. Appl. No. 10/497,900, dated Sep. 8, 2009, 7 pages.

USPTO Notice of Allowance in U.S. Appl. No. 10/497,900, dated Dec. 16, 2009, 7 pages.

Fish & Richardson P.C., Response to Restriction Requirement dated Jan. 25, 2007 in U.S. Appl. No. 10/509,343, filed Feb. 26, 2007, 6 pages.

Fish & Richardson P.C. Amendment in Reply to Action dated May 16, 2007 in U.S. Appl. No. 10/509,343, filed Nov. 16, 2007, 24 pages.

USPTO Interview Summary in U.S. Appl. No. 10/509,343, dated Mar. 6, 2008, 4 pages.

Fish & Richardson P.C. Amendment in Reply to Action dated Feb. 5, 2008 in U.S. Appl. No. 10/509,343, filed Mar. 5, 2009, 10 pages.

USPTO Notice of Allowance in U.S. Appl. No. 10/509,343, dated May 27, 2009, 17 pages.

USPTO Notice of Allowance in U.S. Appl. No. 10/509,343, dated Sep. 21, 2009, 7 pages.

USPTO Notice of Allowance in U.S. Appl. No. 10/509,343, dated Dec. 9, 2009, 5 pages.

Fish & Richardson P.C., Response to Restriction Requirement dated Dec. 28, 2005 in U.S. Appl. No. 10/516,603, filed Mar. 28, 2006, 1 page.
Fish & Richardson P.C., Amendment in Reply to Action dated Apr. 24, 2006 in U.S. Appl. No. 10/516,603, filed Oct. 24, 2006, 9 pages.
Fish & Richardson P.C., Supplemental Response to Amendment filed Oct. 24, 2006 in U.S. Appl. No. 10/516,603, filed Nov. 7, 2006, 5 pages.
Fish & Richardson P.C., Amendment in Reply to Action dated Mar. 9, 2007 in U.S. Appl. No. 10/516,603, filed Jun. 11, 2007, 10 pages.
Fish & Richardson P.C., Amendment in U.S. Appl. No. 10/516,603, filed Sep. 10, 2007, 6 pages.
USPTO Notice of Allowance in U.S. Appl. No. 10/516,603, dated Apr. 25, 2008, 11 pages.
Fish & Richardson P.C., Amendment in U.S. Appl. No. 10/516,603, filed Jul. 24, 2008, 5 pages.
Fish & Richardson P.C., Amendment in Reply to Action dated Jan. 27, 2009 in U.S. Appl. No. 10/516,603, filed May 15, 2009, 4 pages.
USPTO Office Action in U.S. Appl. No. 10/516,603, dated Aug. 19, 2009, 10 pages.
USPTO Interview Summary in U.S. Appl. No. 10/516,603, dated Jan. 8, 2010, 3 pages.
Fish & Richardson P.C., Amendment in Reply to Action dated Aug. 19, 2009 in U.S. Appl. No. 10/516,603, filed Jan. 19, 2010, 7 pages.
USPTO Notice of Allowance in U.S. Appl. No. 10/516,603, dated Feb. 24, 2010, 12 pages.
Fish & Richardson P.C., Amendment in Reply to Action dated Oct. 5, 2007 in U.S. Appl. No. 10/550,987, filed Mar. 5, 2008, 9 pages.
Fish & Richardson P.C., Amendment in Reply to Action dated Mar. 31, 2009 in U.S. Appl. No. 10/550,987, filed Sep. 30, 2009, 6 pages.
USPTO Notice of Allowance in U.S. Appl. No. 10/550,987, dated Nov. 17, 2009, 8 pages.
Fish & Richardson P.C., Amendment in Reply to Action dated Jun. 13, 2008 in U.S. Appl. No. 10/550,987, filed Feb. 19, 2009, 12 pages.
European Search Report for App. Ser. No. EP 03 73 3287, dated Jun. 22, 2009 (2 pages).
European Search Report for App. Ser. No. EP 05 72 7975, dated Sep. 11, 2009, 2 pages.
International Preliminary Report on Patentability for App. Ser. No. PCT/JP2005/006298, dated Feb. 8, 2006, 10 pages.
International Search Report for App. Ser. No. PCT/JP2005/006298, mailed Jul. 12, 2005, 3 pages.
USPTO Notice of Allowance in U.S. Appl. No. 10/550,987, dated Mar. 25, 2010, 5 pages.
USPTO Office Action in U.S. Appl. No. 10/497,900, dated Oct. 30, 2008, 16 pages.
USPTO Office Action in U.S. Appl. No. 10/516,603, dated Jan. 27, 2009, 7 pages.
USPTO Office Action in U.S. Appl. No. 10/550,987, dated Mar. 31, 2009, 12 pages.
Japanese Patent Office, International Preliminary Report on Patentability for App. Ser. No. PCT/JP02/10473, dated Apr. 21, 2003, 4 pages.
Japanese Patent Office, International Search Report for App. Ser. No. PCT/JP02/10473, mailed Feb. 4, 2003, 2 pages.
Japanese Patent Office, International Preliminary Report on Patentability for App. Ser. No. PCT JP02/12708, dated Aug. 12, 2003, 6 pages.
Japanese Patent Office, International Search Report for App. Ser. No. PCT/JP02/12708, mailed Mar. 11, 2003, 4 pages.
Japanese Patent Office, International Preliminary Report on Patentability for App. Ser. No. PCT/JP03/03975, dated Sep. 8, 2003, 6 pages.
Japanese Patent Office, International Search Report for App. Ser. No. PCT/JP03/03975, mailed May 6, 2003, 2 pages.
Japanese Patent Office, International Preliminary Report on Patentability for App. Ser. No. PCT/JP03/07071, dated Nov. 21, 2003, 7 pages.
Japanese Patent Office, International Search Report for App. Ser. No. PCT/JP03/07071, mailed Jul. 22, 2003, 3 pages.
European Search Report for App. Ser. No. EP 04723785.4, dated Jul. 12, 2006, 2 pages.
Japanese Patent Office, International Preliminary Report on Patentability for App. Ser. No. PCT/JP04/004331, dated Dec. 17, 2004, 5 pages.
Japanese Patent Office, International Search Report for App. Ser. No. PCT/JP04/004331, mailed Jun. 22, 2004, 2 pages.

* cited by examiner

|  | 10 64F1 20 30 40 50 60 |
|---|---|
| p64 | GAATTCCACC ATGGTAAGCG CTATTGTTTT ATATGTGCTT TTGGCGGCGG CGGCGCATTC<br>N S T M V S A I V L Y V L L A A A A H S |
|  | 70 80 90 100 110 120 |
| p64 | TGCCTTTGCG GCGGAGCACT GCAACGCGCA AATGAAGACG GGTCCGTACA AGATTAAAAA<br>A F A A E H C N A Q M K T G P Y K I K N |
|  | 130 140 150 160 170 180 |
| p64 | CTTGGACATT ACCCCGCCCA AGGAAACGCT GCAAAGGAC GTGGAAATCA CCATCGTGGA<br>L D I T P P K E T L Q R D V E I T I V E |
|  | 190 200 210 220 230 240 |
| p64 | GACGGACTAC AACGAAAACG TGATTATCGG CTACAAGGGG TACTACCAGG CGTATGCGTA<br>T D Y N E N V I I G Y K G Y Y Q A Y A Y |
|  | 250 260 270 280 290 300 |
| p64 | CAACGGCGGC TCGCTGGATC CCAACACACG CGTCGAAGAA ACCATGAAAA CGCTGAATGT<br>N G G S L D P N T R V E E T M K T L N V |
|  | 310 320 330 340 350 360 |
| p64 | GGGCAAAGAG GATTTGCTTA TGTGGAGCAT CAGGCAGCAG TGCGAGGTGG GCGAAGAGCT<br>G K E D L L M W S I R Q Q C E V G E E L |
|  | 370 380 390 400 410 420 |
| p64 | GATCGACCGT TGGGGCAGTG ACAGCGACGA CTGTTTTCGC GACAACGAGG GCCGCGGCCA<br>I D R W G S D S D D C F R D N E G R G Q |
|  | 430 440 450 460 470 480 |
| p64 | GTGGGTCAAA GGCAAAGAGT TGGTGAAGCG GCAGAATAAC AATCACTTTG CGCACCACAC<br>W V K G K E L V K R Q N N N H F A H H T |
|  | 490 500 510 520 530 540 |
| p64 | GTGCAACAAA TCGTGGCGAT GCGGCATTTC CACTTCGAAA ATGTACAGCA GGCTCGAGTG<br>C N K S W R C G I S T S K M Y S R L E C |
|  | 550 560 570 580 590 600 |
| p64 | CCAGGACGAC ACGGACGAGT GCCAGGTATA CATTTTGGAC GCTGAGGGCA ACCCCATCAA<br>Q D D T D E C Q V Y I L D A E G N P I N |
|  | 610 620 630 640 650 660 |
| p64 | CGTGACCGTG GACACTGTGC TTCATCGAGA CGGCGTGAGT ATGATTCTCA AACAAAAGTC<br>V T V D T V L H R D G V S M I L K Q K S |
|  | 670 680 690 700 710 720 |
| p64 | TACGTTCACC ACGCGCCAAA TAAAAGCTGC GTGTCTGCTC ATTAAAGATG ACAAAAATAA<br>T F T T R Q I K A A C L L I K D D K N N |

FIG. 1-a

|     | 730 | 740 | 750 | 760 | 770 | 780 |
|-----|-----|-----|-----|-----|-----|-----|
| p64 | CCCCGAGTCG | GTGACACGCG | AACACTGTTT | GATTGACAAT | GATATATATG | ATCTTTCTAA |
|     | P   E   S | V   T   R | E   H   C | L   I   D | N   D   I   Y | D   L   S   K |
|     | 790 | 800 | 810 | 820 | 830 | 840 |
| p64 | AAACACGTGG | AACTGCAAGT | TTAACAGATG | CATTAAACGC | AAAGTCGAGC | ACCGAGTCAA |
|     | N   T   W | N   C   K | F   N   R   C | I   K   R | K   V   E | H   R   V   K |
|     | 850 | 860 | 870 | 880 | 890 | 900 |
| p64 | GAAGCGGCCG | CCCACTTGGC | GCCACAACGT | TAGAGCCAAG | TACACAGAGG | GAGACACTGC |
|     | K   R   P | P   T   W   R | H   N   V | R   A   K | Y   T   E | G   D   T   A |
|     | 910 | 920 | 930 | 940 | 950 | 960 |
| p64 | CACCAAAGGC | GACCTGATGC | ATATTCAAGA | GGAGCTGATG | TACGAAAACG | ATTTGCTGAA |
|     | T   K   G | D   L   M | H   I   Q   E | E   L   M | Y   E   N | D   L   L   K |
|     | 970 | 980 | 990 | 1000 | 1010 | 1020 |
| p64 | AATGAACATT | GAGCTGATGC | ATGCGCACAT | CAACAAGCTA | AACAATATGC | TGCACGACCT |
|     | M   N   I | E   L   M | H   A   H   I | N   K   L | N   N   M | L   H   D   L |
|     | 1030 | 1040 | 1050 | 1060 | 1070 | 1080 |
| p64 | GATAGTCTCC | GTGGCCAAGG | TGGACGAGCG | TTTGATTGGC | AATCTCATGA | ACAACTCTGT |
|     | I   V   S | V   A   K | V   D   E   R | L   I   G | N   L   M | N   N   S   V |
|     | 1090 | 1100 | 1110 | 1120 | 1130 | 1140 |
| p64 | TTCTTCAACA | TTTTTGTCGG | ACGACACGTT | TTTGCTGATG | CCGTGCACCA | ATCCGCCGGC |
|     | S   S   T | F   L   S | D   D   T   F | L   L   M | P   C   T | N   P   P   A |
|     | 1150 | 1160 | 1170 | 1180 | 1190 | 1200 |
| p64 | ACACACCAGT | AATTGCTACA | ACAACAGCAT | CTACAAAGAA | GGGCGTTGGG | TGGCCAACAC |
|     | H   T   S | N   C   Y | N   N   S   I | Y   K   E | G   R   W | V   A   N   T |
|     | 1210 | 1220 | 1230 | 1240 | 1250 | 1260 |
| p64 | GGACTCGTCG | CAATGCATAG | ATTTTAGCAA | CTACAAGGAA | CTAGCAATTG | ACGACGACGT |
|     | D   S   S | Q   C   I | D   F   S   N | Y   K   E | L   A   I | D   D   D   V |
|     | 1270 | 1280 | 1290 | 1300 | 1310 | 1320 |
| p64 | CGAGTTTTGG | ATCCCGACCA | TCGGCAACAC | GACCTATCAC | GACAGTTGGA | AAGATGCCAG |
|     | E   F   W | I   P   T | I   G   N   T | T   Y   H | D   S   W | K   D   A   S |
|     | 1330 | 1340 | 1350 | 1360 | 1370 | 1380 |
| p64 | CGGCTGGTCG | TTTATTGCCC | AACAAAAAAG | CAACCTCATA | ACCACCATGG | AGAACACCAA |
|     | G   W   S | F   I   A | Q   Q   K   S | N   L   I | T   T   M | E   N   T   K |
|     | 1390 | 1400 | 1410 | 1420 | 1430 | 1440 |
| p64 | GTTTGGCGGC | GTCGGCACCA | GTCTGAGCGA | CATCACTTCC | ATGGCTGAAG | GCGAATTGGC |
|     | F   G   G | V   G   T | S   L   S   D | I   T   S | M   A   E | G   E   L   A |
|     | 1450 | 1460 s64R1 1470 | 1480 | 1490 | 1500 |
| p64 | CGCTAAATTG | ACTTCGTTCA | TGTTTGGTCA | TGTATAATGA | GAATTC | (SEQ ID NO:9) |
|     | A   K   L | T   S   F | M   F   G   H | V   *   * | E   F | (SEQ ID NO:10) |

FIG. 1-b

TRANSGENIC MICE EXPRESSING BACULOVIRUS SOLUBLE GP64 AND METHODS OF USING SUCH MICE TO MAKE ANTIBODIES

CROSS-REFERENCE TO RELATED APPLICATIONS

This application is the National Stage of International Application No. PCT/JP2005/006298, filed on Mar. 31, 2005, which claims the benefit of Japanese Patent Application Serial No. 2004-107669, filed on Mar. 31, 2004. The contents of both of the foregoing applications are hereby incorporated by reference in their entireties.

TECHNICAL FIELD

The present invention relates to systems and such for antibody production in which animals are immunized with immunogens comprising, other than target antigens, background antigens to produce antibodies specific to the target antigens, and particularly relates to systems and such in which immunized animals carry genes encoding soluble forms of membrane proteins so that immunotolerance against the background antigens comprising the membrane proteins is induced in the immunized animals.

BACKGROUND ART

Antibody production is very difficult when it is difficult to express and purify the target antigens necessary to produce the antibodies. This tendency is pronounced for membrane proteins. Therefore, a technique has been developed which uses proteins that are difficult to express or purify, such as seven-transmembrane proteins, as antigens by expressing the antigenic proteins on the membrane surface of the *Autographa californica* nuclear polyhedrosis virus (AcNPV), which belongs to Baculovirus (Non-Patent Document 1).

However, although baculovirus expression systems are useful as expression systems for various proteins comprising membrane proteins, there are many gp64 membrane proteins (Non-Patent Documents 2 and 3) on the surface of baculoviruses, and these contaminate the expression products obtained from baculovirus expression systems. gp64 is a 64-kDa protein, a major component of the surface of budding viruses, and known to be a protein involved in envelope fusion at low pH. This gp64 is more easily recognized as non-self than human-derived antigenic proteins, and when gp64 contaminates immunogens, antibodies are produced more readily against gp64 than against the target antigens. Therefore, when preparing immunogens using a baculovirus expression system, it is difficult to produce and obtain specific antibodies against antigenic proteins (Non-Patent Document 4). As a means to solve this problem, the present inventors generated gp64 transgenic mice (hereinafter referred to as "Tgm"). Before their immune system develops, these Tgm (hereinafter referred to as "gp64Tgm") carry an exogenous gp64 in the same way as the endogenous genes. Therefore, these Tgm show immunotolerance against gp64, just as they do for the endogenous genes. Thus they recognize target antigenic proteins expressed using baculovirus, enabling the advantageous production of specific antibodies (Patent Document 1).

However, the gp64Tgm showed a phenotype with no testes development nor sperm formation. Therefore, the maintenance of the strain was restricted to females, and although the strain could be maintained, efficient breeding was not possible. In addition, there were some difficulties when producing crossbred animals by crossing with other knockout mice or Tgm.

[Patent Document 1] WO 03/104453.
[Non-Patent Document 1] Biotechnology, vol. 13, 1079-84, 1995.
[Non-Patent Document 2] Journal of Immunological Methods, vol. 234, 123-135, 2000.
[Non-Patent Document 3] Journal of Virology, vol. 70, No. 7, 4607-4616, 1996.
[Non-Patent Document 4] Journal of Virology, vol. 69, No. 4, 2583-2595, 1995.

DISCLOSURE OF THE INVENTION

Problems to be Solved by the Invention

As described above, the aforementioned gp64Tgm are useful as animals to be immunized for producing specific antibodies against proteins expressed using baculoviruses, but gp64Tgm had a problem of being infertile. Therefore, an objective of the present invention is to generate even more useful Tgm without unfavorable phenotypes such as inhibited testes development, and to provide methods and such for producing antibodies using these novel Tgm, so that the expression and maintenance of such exogenous membrane proteins in transgenic animals are enabled.

Means to Solve the Problems

The present inventors predicted that the inhibition of testes development is caused by gp64 expression on cell membranes in the testes. Soluble gp64 (hereinafter referred to as "sgp64"), produced by deleting the transmembrane region from (full-length) gp64, was linked to the pCAGGS vector (Gene, vol. 108, 193-200, 1991) to construct an sgp64 expression vector (hereinafter referred to as "pCAG-sgp64 vector"). When sgp64Tgm were produced by introducing this vector into mice, male Tgm maintained their fertility, and the present inventors successfully overcame the conventional problem of inhibited testes development. These sgp64Tgm and control non-transgenic mice were immunized using a budding baculovirus, sera were collected, and the presence of immunotolerance against gp64 was examined. As a result, antibodies against gp64 were produced in control non-transgenic mice, but were hardly detected in sgp64Tgm. In other words, the present inventors were able to avoid the male infertility observed in conventional gp64Tgm by using sgp64, and were able to establish transgenic mice effective for producing antibodies using antigens expressed in baculovirus. The present invention is based on these findings, and more specifically, relates to the following:

(1) a nonhuman animal carrying a gene encoding a soluble form of a membrane protein;
(2) the nonhuman animal of (1), which is a transgenic animal into which a gene encoding a soluble protein (also referred to as "soluble form protein" in the present application) has been introduced exogenously;
(3) the nonhuman animal of (2), which is a progeny of the transgenic animal into which a gene encoding a soluble protein has been introduced exogenously;
(4) the nonhuman animal of any one of (1) to (3), wherein the membrane protein is derived from a virus;
(5) the nonhuman animal of (4), wherein the virus is a baculovirus;

(6) the nonhuman animal of (5), wherein the membrane protein is gp64;
(7) the nonhuman animal of (6), wherein the soluble protein is gp64 that lacks a transmembrane region;
(8) the nonhuman animal of (6), wherein the soluble protein comprises an extracellular region of gp64;
(9) the nonhuman animal of any one of (1) to (8), wherein the nonhuman animal is a mouse;
(10) the nonhuman animal of any one of (6) to (9), wherein the male is fertile;
(11) a method for producing an antibody, which comprises the steps of:
  immunizing the nonhuman animal of any one of (1) to (10) with an immunogen comprising a target antigen; and
  obtaining an antibody against the target antigen or a gene encoding such an antibody;
(12) the method of (11) for producing an antibody, wherein the immunogen is a viral particle or a portion thereof;
(13) the method of (12) for producing an antibody, wherein the virus is a baculovirus;
(14) the method of any one of (11) to (13) for producing an antibody, wherein the target antigen is a membrane protein; and
(15) a system for producing an antibody, which comprises the nonhuman animal of any one of (1) to (10).

To facilitate the understanding of the present invention, the meaning of some of the presupposed terms are explained.

In the present invention, the term "target antigen" denotes antigens recognized by subject antibodies. The target antigens can be selected from any substance having antigenicity. Specifically, proteins, sugar chains, lipids, inorganic substances, or such are known as substances showing antigenicity. The target antigens may be naturally occurring or artificially synthesized. The artificially synthesized target antigens comprise recombinant proteins prepared by genetic engineering technology, and many kinds of chemically-synthesized organic compounds.

The term "background antigen" denotes substances comprising antigenic determinants for which antibody generation is not desired, or denotes the antigenic determinants themselves. For example, any antigenic substance that is not a target antigen, but which contaminates the target antigen, is a background antigen. Typical background antigens are proteins contaminated within crudely purified target antigens. More specifically, host cell-derived proteins in a recombinant protein are examples of background antigens. The term "background antigen" may also be defined to mean antigens that are comprised within an immunogen for inducing subject antibody generation, and that induce production of a non-subject antibody. Generally, a background antigen is thought to indicate an antigenic substance other than a target antigen. In the present invention, however, antigenic determinants present on target antigen molecules may also be comprised in the background antigens. For example, if an antigenic determinant for which antibody generation is undesired is present on a target antigen molecule, the antigenic determinant is comprised in the background antigens of the present invention.

The term "immunotolerance" denotes a condition in which an immune response, specific to an antigen that is an immunotolerance target (an immunotolerance antigen), is lost or decreased. When the level of a subject's immune response to an immunotolerance antigen is reduced compared to that of a normal immunized animal, the subject can be regarded to comprise immunotolerance against the immunotolerance antigen. For example, when the amount of an antibody generated against an immunotolerance antigen is decreased in response to the administration of an immunotolerance antigen, the level of immune response is then considered to be low.

BRIEF DESCRIPTION OF THE DRAWINGS

FIG. 1-a shows the nucleotide sequence of the soluble gp64 gene used in the Examples. Nucleotides 1 to 720 are shown.

FIG. 1-b shows the nucleotide sequence of the soluble gp64 gene used in the Examples. Nucleotides 721 to 1486 are shown.

DETAILED DESCRIPTION

Figure 2:
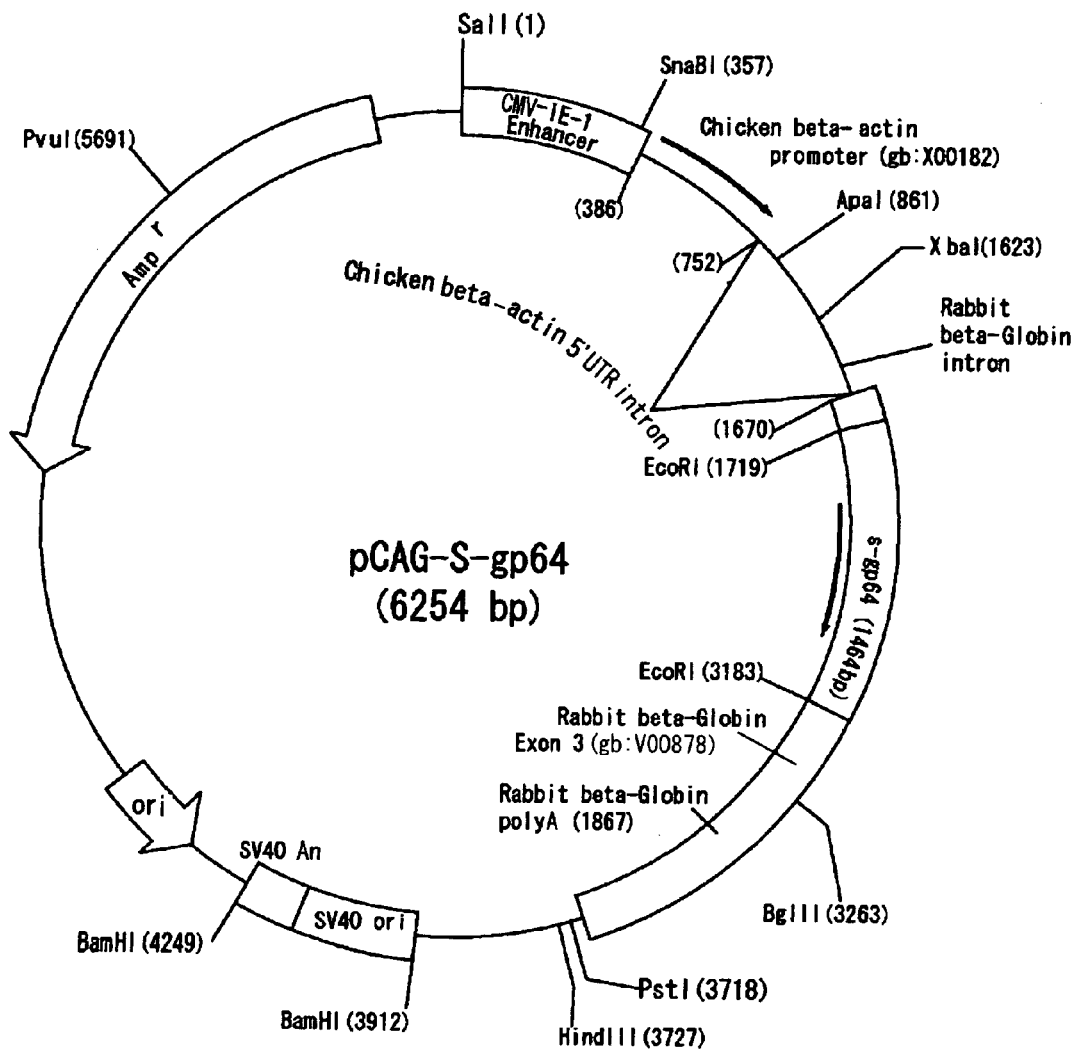
FIG. 2 shows a schematic map of the pCAG-sgp64 vector.

The present invention provides transgenic animals useful for producing antibodies against target antigens when using immunogens that have, other than the target antigens, membrane proteins contaminating as background antigens, and also provides methods and systems for antibody production using such transgenic animals.

As described above, in the present invention, the background antigens are membrane proteins. Examples of cases where membrane proteins contaminate as background antigens comprise the contamination of membrane proteins derived from host organisms used to prepare target antigens, and the contamination of membrane proteins derived from viruses used for the expression systems. For example, when the target antigen is expressed together with viral vector-derived membrane proteins, such as the case in which a baculovirus expression system is used to prepare a membrane protein as a target antigen, large quantities of vector-derived membrane proteins contaminate as background antigens.

Herein, "membrane protein" ordinarily means a protein that constitutes a biological membrane, and for example, it refers to a protein embedded in a biological membrane; however, in the present invention, it also comprises proteins linked to a cell membrane surface via an anchor and the like, such as GPI-anchored proteins. Moreover, virus-derived membrane proteins ordinarily refer to proteins that constitute the envelope of budding viruses. For example, in baculoviruses, a protein called gp64 corresponds to a membrane protein. The structure of many of these membrane proteins comprises a region embedded in the cell membrane (transmembrane region), a region exposed on the outer side of the cell membrane (extracellular region), and a region positioned on the inner side of the cell membrane (intracellular region). Functionally, membrane proteins comprise proteins constituting membranes, receptors, proteins involved in signal transduction and the like such as transporters, and proteins such as membrane enzymes that perform specific reactions. Therefore, when such an exogenous membrane protein is introduced into an animal to be immunized, its expression in any biological membrane of the animal to be immunized will not only induce immunotolerance, but may also confer other unfavorable characteristics. For example, the problem of male infertility arises in mice into which the baculovirus-derived membrane protein gp64 has been introduced.

In the nonhuman animals of the systems for antibody production of the present invention, immunotolerance is induced against virus-derived membrane proteins that may be contaminating immunogens as the aforementioned background antigens. For example, nonhuman animals in which immunotolerance against baculovirus-derived membrane protein gp64 has been induced are used as the immunized animals when using immunogens prepared with the baculovirus expression systems. In the past, methods where immunized animals carry a gene encoding a full-length membrane protein, which is a background antigen, had been developed as methods for inducing immunotolerance; however, in the present invention, nonhuman animals carry a gene encoding a solubilized membrane protein (hereinafter referred to as a "soluble protein").

A "soluble protein" (also referred to as "soluble form protein" in the present application) refers to a membrane protein originally expressed on a biological membrane (insoluble protein) that has been modified so that it may be expressed outside a biological membrane. As described above, since membrane proteins comprise those that function as receptors or transporters that may be involved in signal transduction and those that function as switches in the living body, such as membrane enzymes, when such membrane proteins are expressed in the biological membranes of the animals to be immunized, they not only induce immunotolerance against background antigens in the animals to be immunized but can also confer unfavorable characteristics to the animals. To avoid such inconveniences, in the present invention, the membrane proteins are converted to soluble forms so that they may be expressed outside biological membranes. In addition, compared to conventional methods that use full-length membrane proteins and express them on biological membranes, which are localized sites, the present invention allows membrane proteins to be expressed systemically in the cytoplasm in their soluble form; therefore, the efficiency of immunotolerance induction is expected to improve.

In the present invention, genetic engineering methods for modifying genes encoding membrane proteins are used to modify the membrane proteins into soluble forms. An example of a genetic engineering method for solubilizing membrane proteins is the deletion of a transmembrane region. The degree of transmembrane region deletion may be deletion of a portion of the transmembrane region, or deletion of the entire transmembrane region, so long as the membrane protein can be expressed extracellularly. Since transmembrane regions generally form an α-helical structure comprising 20 to 30 amino acids, proteins can also be solubilized by introducing mutations to change this structure.

As regions other than the transmembrane region, there are the intracellular region and the extracellular region; however, when modifying membrane proteins into soluble proteins, the intracellular region is not necessary, and soluble proteins may be limited to the extracellular region alone, which is equipped with antigenic determinants that can induce immunotolerance. Moreover, the extracellular region may also be limited to regions that may induce immunotolerance, such as regions that maintain antigenicity and are equipped with antigenic determinants capable of inducing immunotolerance against membrane proteins.

In addition to deleting the transmembrane region and such from membrane proteins and such, the aforementioned soluble proteins may comprise a chimeric protein into which other peptides and such have been added or inserted. The peptides added/inserted to the chimeric proteins may be antigenic determinants of other background antigens (these "other background antigens" may or may not be membrane proteins). Thus, immunotolerance against multiple background antigens can be induced by equipping a single protein with antigenic determinants against multiple background antigens.

As an example of the construction of a soluble protein, the case of baculovirus membrane protein gp64 will be used and explained. gp64 is encoded by the DNA sequence of SEQ ID NO: 1; its transmembrane region is encoded by nucleotides 1465 to 1515, and its extracellular region is encoded by nucleotides 1 to 1464. Therefore, to solubilize gp64, the aforementioned transmembrane region can be deleted, the sequence encoding the amino acids responsible for the α-helix structure can be substituted with that of other amino acids, or so forth. Also, the entire protein, comprising 488 amino acid residues that are encoded by nucleotides 1 to 1464 shown in SEQ ID NO: 3, may be used for the aforementioned extracellular region, or the length of the extracellular region can be shortened to within a range that can maintain cross-reactivity with gp64 and induce immunotolerance against gp64. Furthermore, one or more modifications such as amino acid deletion, substitution, addition, or insertion can be made to the amino acid sequence of the extracellular region of gp64 (amino acid residues 1 to 488 in the amino acid sequences of SEQ ID NOs: 1 to 3), within a range that allows the induction of immunotolerance against gp64 in the immunized animals described below.

In the present invention, immunotolerance is induced by making nonhuman animals carry genes encoding such soluble proteins. Nonhuman animals that can be used in the present invention comprise, for example, monkeys, pigs, dogs, rats, mice, and rabbits. For example, rodents such as rats, mice, and hamsters are preferable as nonhuman animals. To induce immunotolerance by preparing transgenic animals, it is advantageous to use nonhuman animals which mature fast and for which gene manipulation technologies have been established, such as rodents. Mice in particular are nonhuman animals that meet these requirements at a high level.

Nonhuman animals carrying a gene encoding the aforementioned soluble protein can be obtained by producing transgenic animals into which a gene encoding the soluble protein has been introduced as an exogenous gene. For example, transgenic mice can be produced according to known methods (Proc. Natl. Acad. Sci. USA 77: 7380-7384 (1980)). Specifically, subject genes are introduced into mammalian totipotent cells, and then the cells are brought up into individuals. A subject transgenic mouse can be obtained from the individuals thus obtained by screening for individuals in which the introduced gene has been integrated into both somatic cells and germ cells. Fertilized eggs, early embryos, and cultured cells with multipotency such as ES cells, and such, can be used as the totipotent cells for introducing a gene. More specifically, they can be produced by the method in the Examples described below.

The nonhuman animals carrying a gene encoding a soluble protein of the present invention may be offspring of the above-mentioned transgenic animals. Once transgenic animals are established, transmission to the offspring of the characteristics (in the present invention, the characteristic of immunotolerance) caused by the introduced gene is usually easy. However, since the previously developed transgenic animals into which baculovirus gp64 has been introduced had developed the problem of male infertility, it was difficult to efficiently reflect the characteristic of immunotolerance in their offspring. On the other hand, in the present invention, by producing transgenic animals using genes encoding soluble forms of the membrane proteins, the expression of unfavorable characteristics found in the transgenic animals into which genes encoding full-length membrane proteins have been introduced was avoided. As one example, the use of a gene encoding a soluble form of the baculovirus gp64 protein in the production of transgenic animals has made it simple to transmit characteristics to the offspring by maintaining male fertility and efficient reproduction. Since transgenic animals carrying soluble gp64 can reproduce efficiently, and their offspring also carry the characteristic of immunotolerance, they become useful as animals to be immunized for antibody production and such, as described below. Therefore, by making nonhuman animals carry a gene encoding a soluble protein rather than a full-length membrane protein, immunized animals in which immunotolerance has been induced against that membrane protein can be more widely and easily used.

Nonhuman animals carrying a gene encoding a soluble form of a membrane protein of the present invention can be produced based on gene deficient animals in which the target antigenic protein is deleted (so-called knockout animals). Nonhuman animals carrying a gene encoding the soluble form of the membrane protein may also be produced by crossing background antigen-expressing transgenic animals with such target antigenic protein knockout animals. This enables the characteristics of background antigen expression and target antigenic protein deletion to be conferred to the nonhuman animals. In such animals carrying both characteristics, immunotolerance against background antigens is induced, while the target antigen is more readily recognized as a foreign substance since the animals do not innately carry the target antigen; therefore, the desired antibodies can be obtained efficiently.

In the nonhuman animals of the present invention, in which immunotolerance against background antigens is induced, suppression of antibody production against all background antigens that may be comprised in an immunogen is not necessarily important. Production of antibodies that recognize background antigens is tolerated if it is within a range that does not interfere with production and collection of antibodies against the target antigen. Therefore, for example, even animals to be immunized in which immunotolerance has been induced against only the major background antigens may be utilized as favorable immunized animals of the present invention.

The present invention relates to methods for producing antibodies by utilizing nonhuman animals that carry genes encoding the abovementioned soluble forms of membrane proteins.

These methods comprise the step of immunizing nonhuman animals carrying a gene encoding the abovementioned soluble form of a membrane protein with an immunogen comprising, other than a target antigen, this membrane protein as a background antigen, and the step of obtaining antibodies against the previously-described target antigen or genes encoding these antibodies.

The immunogens of the present invention comprise, other than a target antigen, at least a membrane protein as a background antigen. Generally, a target antigen comprises substances derived from biological materials. Biological materials are complex mixtures comprising various components. Thus, target antigens are usually prepared using various mixtures as starting materials. Therefore, it is difficult to obtain highly-purified target antigens. In other words, it involves a lot of time and effort to isolate a large quantity of a highly pure target antigen. The present invention provides methods that enable efficient acquisition of antibodies against target antigens using such immunogens which have, other than a target antigen, membrane proteins contaminating as background antigens.

More specifically, examples of the immunogens of the present invention comprise cells, cell culture solutions, cell lysates, viruses, and crude antigens, in which membrane proteins may be contaminating as background antigens. When using cells or viruses, a gene encoding a desired antigen can be introduced into the cells or viruses by gene recombination techniques, and those that artificially express the desired antigen can be used. Whole cells or viruses as well as portions thereof can be used as the immunogens. Furthermore, just cell membrane or viral envelope portions may be used as the immunogens. When such whole cells or viruses, or portions thereof, such as their cell membrane or viral envelope, are used as the immunogen, membrane proteins comprised in the cell membrane or viral envelope contaminate as background antigens.

One preferable immunogen of the present invention is a viral particle or portion thereof. Viruses are comprised of relatively simple components, including nucleic acids, and limited proteins, saccharides, and such. Consequently, the types of background antigens that may interfere with target antigen acquisition are also limited. Background antigens from viral particles or portions thereof that interfere with the acquisition of target antigen comprise membrane proteins on the surface of the particles. When administered to the animals to be immunized, the particle surfaces are highly antigenic, and can readily induce antibody production. Therefore, the methods for producing antibodies based on the present invention can be carried out more favorably if, even from among these few background antigens, immunotolerance in the animals to be immunized is induced against background antigens that are membrane proteins on the particle surface and the like.

In the present invention, baculovirus is one among the preferred among the viruses that can be used as immunogens. Baculoviruses are insect viruses that comprise a structure whereby a double-stranded DNA genome is covered with a capsid protein. Expression systems using Nucleopolyhedrovirus (NPV), a type of baculovirus, are useful as systems for expressing exogenous genes. NPV comprises strong promoter activity. Therefore, any protein can be produced in large quantities by inserting an exogenous gene into the NPV genome. Specifically, strong expression of any exogenous gene is induced by recombinantly substituting the gene coding for the protein called polyhedron with the exogenous gene.

The foreign genes that are expressed in the aforementioned baculovirus expression systems are not particularly limited, and any gene may be used; however, since baculoviruses can be utilized as systems suitable for expressing membrane proteins, an example of a suitable gene is a gene encoding a membrane protein. In the baculovirus expression systems, a subject membrane protein can be expressed along with a baculovirus envelope protein in a form that retains its structure. Another advantage of the baculovirus expression systems is that the expression products can be easily recovered as budding viral particles.

As methods for expressing membrane proteins which are the target antigens using baculoviruses, for example, the method using budding baculoviruses described in WO 98/46777 and Loisel et al. (Loisel, T. P. et al., Nature Biotech. 15: 1300-1304 (1997)) can be used. More specifically, a recombinant vector for insect cells comprising a gene encoding an exogenous protein is constructed, and introduced, along with baculoviral DNA, into insect cells such as Sf9. The exogenous membrane protein encoded by the recombinant vector is expressed on mature viral particles (virions), which are released by infected cells to the outside of cells prior to infected cell death. Recombinant viruses that express the exogenous protein can thus be obtained.

In the present invention, a budding virus is a virus that is released from infected cells by budding. Generally, viruses covered with an envelope can bud from cells infected with these viruses, and are released continuously, even when the cells have not been destroyed. On the other hand, adenoviruses that are not covered by an envelope, and herpes viruses that are covered by a nuclear envelope, are released from the cells all at once, upon cell destruction. Budding viruses are particularly preferable in the present invention. In addition, those skilled in the art can suitably select hosts to be infected with a recombinant virus, depending on the type of virus used, so long as viral replication is possible in the host. For example, insect cells such as Sf9 cells can be used when using baculoviruses. Generally, protein expression systems using baculoviruses and insect cells are considered to be useful systems because modifications that occur at the same time as translation or post-translationally, such as fatty acid acetylation or glycosylation, are carried out in the same way as with mammalian cells and because the expression level of heterologous proteins in such systems is greater than that in mammalian cell systems (Luckow V. A. and Summers M. D., Virol. 167: 56 (1988)).

The viruses expressing exogenous proteins, which are the target antigens, can be obtained by, for example, culturing a host that has been infected with a recombinant virus comprising a gene that encodes an exogenous protein. Alternatively, using methods such as the above-mentioned methods of WO 98/46777 and Loisel et al (Loisel, T. P. et al., Nature Biotech. 15: 1300-1304 (1997)), a recombinant vector encoding an exogenous protein can be introduced into an insect cell along with a baculovirus, and exogenous proteins can be expressed on the envelope of the baculovirus released outside of the cell. In addition, using methods like that of Strehlow et al. (D. Strehlow et al., Proc. Natl. Acad. Sci. USA. 97: 4209-4214 (2000)), packaging cells such as PA317 can be infected with recombinant Moloney murine leukemia viruses, which are constructed using vectors derived from Moloney viruses into which exogenous protein-encoding genes have been introduced, and the exogenous proteins can be expressed on the envelope of viruses released outside of the cells. These are examples of viruses for expressing exogenous proteins and the viruses of the present invention that express exogenous proteins, useful as immunogens, are not limited to those that are constructed using the above methods.

Recombinant viruses constructed as described above can be purified using known methods, as necessary. For example, known methods for purifying viruses comprise augmented density gradient centrifugation (Albrechtsen et al., J. Virological Methods 28: 245-256 (1990); Hewish et al., J. Virological Methods 7: 223-228 (1983)), size exclusion chromatography (Hjorth and Mereno-Lopez, J. Virological Methods 5: 151-158 (1982); Crooks et al., J. Chrom. 502: 59-68 (1990); Mento S. J. (Viagene, Inc.) 1994 Williamsburg Bioprocessing Conference), affinity chromatography using monoclonal antibodies, sulphated fucose-containing polysaccharides and the like (Najayou et al., J. Virological Methods 32: 67-77 (1991); Diaco et al., J. Gen. Virol. 67: 345-351 (1986); Fowler, J. Virological Methods 11: 59-74 (1986); Japanese Patent Saikohyo Publication No. (JP-A) 97/032010 (unexamined Japanese national phase publication corresponding to a Japanese international publication)), and DEAE ion exchange chromatography (Haruna et al., Virology 13: 264-267 (1961)). Thus, purification can be carried out using the above methods or combinations thereof.

Animals to be immunized are immunized using immunogens prepared as described above. The immunized animals used in the present invention are nonhuman animals in which immunotolerance against a background antigen membrane protein comprised in an immunogen has been induced. Induction of immunotolerance against a background antigen membrane protein can be carried out as described above, by making animals to be immunized carry a gene encoding a soluble form of this membrane protein.

When a baculovirus expression system, which was shown above as an expression system suitable for membrane protein preparation, is used for immunogen preparation, preferably, nonhuman animals made to carry a gene encoding a soluble gp64 and induced to have immunotolerance against gp64 are used as the immunized animals. Herein, nonhuman animals carrying a gene encoding the full-length gp64 may be used as the immunized animals, however, the use of soluble gp64 transgenic animals and such is preferred since they can be widely used, and can be produced efficiently since both males and females are fertile. Therefore, for example, in a preferred embodiment of the present invention, nonhuman animals carrying a gene encoding a soluble gp64 are used as immunized animals, and a budding baculovirus made to express a membrane protein as the target antigen is used as the immunogen to carry out the immunizations.

By using the antibody-production methods of the present invention, the inhibitory effect on the acquisition of antibodies against a target antigen due to contamination of membrane proteins as background antigens can be suppressed. Consequently, the use of this invention enables sufficient application of the advantages of a baculovirus expression system as an exogenous protein expression system, even in the preparation of immunogens.

Well-known methods can be used for the methods of immunizing to obtain antibodies. Animals can be immunized with an immunogen using known methods. General methods comprise injecting a sensitizing antigen into a mammal by subcutaneous or intraperitoneal injection. Specifically, an immunogen is diluted with an appropriate volume of Phosphate-Buffered Saline (PBS), physiological saline, or such and as desired, the suspension is mixed with an appropriate volume of a conventional adjuvant. This is emulsified and administered to the mammals. For example, Freund's complete adjuvant can be used as an adjuvant. In addition, after this, an immunogen that has been mixed with an appropriate volume of Freund's incomplete adjuvant is preferably administered several times every four to 21 days. In this way immunization occurs, and the increased level of a desired antibody in the serum can be confirmed using conventional methods.

An increase in the level of a desired antibody in the serum is confirmed, blood is collected from the immunized mammals, and the serum is separated. As polyclonal antibodies, serum comprising polyclonal antibodies can be used. Where necessary, fractions comprising polyclonal antibodies can be isolated from this serum, and this fraction can also be used.

Methods for producing monoclonal antibodies can be combined with the antibody production methods of the present invention. After confirming the increase in the level of the intended antibody in the serum of a mammal that was sensitized by the above-described antigen, the antibody-producing cells are extracted from the mammal and cloned to obtain monoclonal antibodies. Spleen cells and such can be used as antibody-producing cells. Antibody-producing cells can be cloned by cell fusion methods. Mammalian myeloma cells and such can be used as parent cells to be fused with the above-mentioned antibody-producing cells. Even more preferably, myeloma cells that comprise unique auxotrophy or drug resistance can be examples of useful selective markers for fusion cells (hybridoma cells). By basically following the methods known in the art, fusion cells can be obtained from the antibody-producing cells and the myeloma cells described above. Methods for producing monoclonal antibodies by using the cell fusion techniques have been established, for example, by Milstein et al. (Galfre, G. and Milstein, C., Methods Enzymol. (1981) 73, 3-46).

The hybridoma cells produced by cell fusion techniques are selected by culturing in a selective medium. A selective medium is chosen in accordance with the characteristic features and such of the myeloma cells used for the cell fusion. HAT medium (a medium comprising hypoxanthine, aminopterine, and thymidine), for example, can be used as a selective medium. The hybridoma cells are cultured in the HAT medium for a time sufficient to kill all cells other than the intended hybridoma cells (e.g. all non-fused cells). Generally, hybridoma cells can be selected by continuing culture for several days to several weeks. Then, a standard limiting dilution method is carried out to screen and clone the hybridoma cells that produce the subject antibodies.

Subsequently, the hybridoma cells thus obtained can be intraperitoneally transplanted into mice to obtain ascites fluid comprising the monoclonal antibodies. Monoclonal antibodies can also be purified from the ascites fluid. For example, monoclonal antibodies can be purified by ammonium sulfate precipitation methods, protein A or protein G columns, DEAE ion exchange chromatography, or affinity columns coupled with a target antigen.

Monoclonal antibodies obtained in this way can also be made into recombinant antibodies produced using gene recombination technologies (for example, see Borrebaeck, C. A. K. and Larrick, J. W., Therapeutic Monoclonal Antibodies, UK, Macmillan Publishers Ltd., 1990). Recombinant antibodies are produced by cloning the DNAs that encode them from antibody-producing cells, such as hybridomas and antibody-producing sensitized lymphocytes, then incorporating these DNAs into a suitable vector, and introducing this vector into a host.

Furthermore, antibody fragments and modified antibodies can be obtained by combining antibody alteration and modification techniques with the antibody production method of the present invention. For example, an antibody fragment can be an Fab, F(ab')2, Fv, or a single chain Fv (scFv) where the Fvs of an H chain and L chain are linked by a suitable linker (Huston, J. S. el al., Proc. Natl. Acad. Sci. U.S.A., (1988) 85, 5879-5883). Antibodies bound to various molecules such as polyethylene glycols (PEG), can also be used as the modified antibodies. Such modified antibodies can be obtained by chemically modifying the obtained antibodies. These methods have already been established in the art.

The methods for producing antibodies of the present invention can be combined with modification techniques used for human antibodies. Human antibodies of interest can be obtained by using transgenic animals carrying the complete repertoire of human antibody genes as a basis (see International Patent Application Publication Nos. WO 93/12227, WO 92/03918, WO 94/02602, WO 94/25585, WO 96/34096, and WO 96/33735), introducing a gene encoding a soluble form of a background antigen, making them carry the ability to produce human antibodies and the immunotolerance against the background antigen, and immunizing them with a desired antigen.

The antibodies obtained by the methods of the present invention can be chimeric antibodies comprising non-human antibody-derived variable regions, derived from the immunized animals, and human antibody-derived constant regions. In addition, they can also be humanized antibodies comprising complementarity determining regions (CDRs) of non-human antibodies derived from the immunized animals and the framework regions (FRs) and constant regions derived from human antibodies. These modified antibodies can be produced using known methods. Specifically, for example, a chimeric antibody is an antibody comprising the antibody heavy chain and light chain variable regions of an immunized animal, and the antibody heavy chain and light chain constant regions of a human. A chimeric antibody can be obtained by (1) ligating a DNA encoding a variable region of an immunized animal-derived antibody to a DNA encoding a constant region of a human antibody; (2) incorporating this into an expression vector; and (3) introducing the vector into a host for production of the antibody.

A humanized antibody, which is also called a reshaped human antibody, is a modified antibody. A humanized antibody is constructed by transplanting a complementarity determining region (CDR) of an antibody derived from an immunized animal, into the CDR of a human antibody. Conventional genetic recombination techniques for the preparation of such antibodies are known.

Specifically, a DNA sequence designed to ligate a mouse antibody CDR with a human antibody framework region (FR) is synthesized by PCR, using several oligonucleotides constructed to comprise overlapping portions at their ends. A humanized antibody can be obtained by (1) ligating the resulting DNA to a DNA which encodes a human antibody constant region; (2) incorporating this into an expression vector; and (3) introducing the vector into a host to produce the antibody (see, European Patent Application Publication No. EP 239,400, and International Patent Application Publication No. WO 96/02576). Those human antibody FRs that are ligated via the CDR, such that the CDR forms a favorable antigen-binding site, are selected. As necessary, amino acids in the framework region of an antibody variable region may be substituted such that the CDR of a reshaped human antibody forms an appropriate antigen-binding site (Sato, K. et al., Cancer Res. (1993) 53, 851-856).

Furthermore, genes coding for the antibodies can be obtained from the antibody-producing cells of an immunized animal. Methods used to obtain genes that code for antibodies are not limited. For example, genes coding for antibodies can be obtained by amplification using the PCR method, by using as templates those genes that code for variable regions or CDRs. Primers for the amplification of genes that code for antibodies are known in the art. Subject antibodies can be produced by expressing genes thus obtained in an appropriate expression system. Alternatively, the genes obtained by the present invention can be utilized to produce various modified antibodies (chimeric antibodies comprising human antibody-derived constant regions and humanized antibodies in which the CDRs of an immunized animal-derived antibody is transplanted to the CDRs of a human antibody).

The present invention provides systems for antibody production that comprise nonhuman animals carrying a gene encoding a soluble form of a membrane protein.

When an immunogen is prepared using a viral expression vector, in certain cases, membrane proteins derived from that virus or from host cells into which the viral expression vector has been introduced may contaminate as background antigens. These background antigen membrane proteins are not products of the exogenous target antigen gene, and in most cases, they are derived from the expression system, such as from the vector or host. Therefore, the background antigen membrane proteins that may contaminate are identified for every expression system. Then, a gene encoding a soluble form of this membrane protein is introduced into nonhuman animals by transgenic techniques, and whether immunotolerance against the membrane protein has been induced is confirmed in the obtained transgenic animals. Whether or not immunotolerance has been induced in the nonhuman animals can be confirmed as indicated in the Examples, by confirming the production of antibodies against the background antigen membrane protein in the serum.

Because the background antigen membrane protein is expressed in its soluble form, the expression of unfavorable phenotypes, such as the loss of fertility in males observed with the baculovirus gp64, is avoided in these nonhuman animals in which the induction of immunotolerance against the background antigen has been confirmed; such animals may thus be provided as widely useful animals to be immunized. Therefore, systems that can support efficient antibody production can be constructed by combining the animals to be immunized that carry a gene encoding a soluble form of a membrane protein of the present invention with an expression system that produces this membrane protein as a background antigen.

For example, by combining a baculovirus expression system described in detail above with nonhuman animals carrying a gene encoding a soluble gp64, the advantages of a baculovirus expression system can be reflected in antibody production. More specifically, in a baculovirus expression system, desired proteins, particularly membrane proteins, can be expressed as target antigens along with gp64 while maintaining their three-dimensional structure, and the expression products can be easily collected as budding viruses. These budding viruses are used as the immunogens and immunization is performed on the nonhuman animals carrying a gene encoding a soluble gp64 as the immunized animals. Since immunotolerance against gp64 is induced in these nonhuman animals carrying a gene encoding a soluble gp64, even if a large amount of gp64 is expressed on the budding virus serving as the immunogen, antibody production against this gp64 is suppressed and antibodies against the membrane protein serving as the target antigen can be produced. Therefore, even when gp64 is present on a baculovirus as a background antigen, by using nonhuman animals carrying a gene encoding a soluble gp64, antibody production against the target antigen can be favorably induced. As a result, the antibodies obtainable by the present system will be extremely pure antibodies against the target antigen.

All prior art references cited herein are incorporated by reference into this description.

EXAMPLES

Example 1

Construction of an sgp64 Transgenic Vector

The transmembrane region (nucleotides 1465 to 1539) was deleted from the gp64 gene (SEQ ID NO: 1; full length: 1539 bp) to prepare by PCR a gene fragment comprising only the extracellular region (soluble gp64; 1464 bp; SEQ ID NO: 3).

More specifically, a 5' primer in which the 5'-terminal sequence of gp64, the restriction enzyme EcoRI recognition sequence, and a KOZAK sequence are linked (64F1: 5'-GAATTCCACCATGGTAAGCGCTATTGTT-3'; SEQ ID NO: 5); a 3' primer in which the EcoRI recognition sequence is 5'-end linked to the sequence immediately before the transmembrane region of gp64 (s64R1: 5'-GAATTCTCATTATA-CATGACCAAACATGAACGA-3'; SEQ ID NO: 6) (FIG. 1-a and FIG. 1-b); and the pCAG-gp64 vector serving as a template DNA were used, and a polymerase chain reaction (PCR) was performed under the following conditions: the composition of the PCR reaction solution was 5 µL of 10× ExTaq buffer (TaKaRa), 4 µL of dNTP mixture comprised in the ExTaq kit, 1 µL of 64F1 primer (10 µmole/L), 1 µL of s64R1 primer (10 µmole/L), 1 µL of pCAG-gp64 (500 pg/µL), 0.5 µL of ExTaq (5 units/µL, TaKaRa), and 37.5 µL of $H_2O$. The reaction was carried out by heating at 94° C. for five minutes, and then performing 25 cycles of 94° C. for 15 seconds, 57° C. for 30 seconds, and 72° C. for 30 seconds. The mixture was then treated at 72° C. for seven minutes, and stored at 4° C. The amplified band was subcloned into pGEM-Teasy (Promega) and E. coli (DH5α, TOYOBO) were transformed with this. Colony PCR was performed using the T7 primer (5'-TAATACGACTCACTATA-3', SEQ ID NO: 7) and SP6 primer (5'-CATACGATTTAGGTGACACTATAG-3', SEQ ID NO: 8), the nucleotide sequences of clones found to carry the insert were analyzed with an ABI Prism 377 DNA sequencer using the BigDye Cycle Sequence kit (Applied Biosystems) and the T7 primer or the SP6 primer, and a clone carrying the desired gene was confirmed. The fragment comprising gp64 was cut out from this clone by EcoRI restriction enzyme treatment, inserted into pCAGGS vector treated with the restriction enzyme EcoRI, and E. coli (DH5α) were transformed with this. The direction of insertion of the gp64 fragment was determined from the size of the band (approximately 2.1 kb) obtained by XhoI and XbaI restriction enzyme treatment and the pCAG-sgp64 vector was produced (FIG. 2). The clone as designed was cultured overnight at 37° C. using 250 mL of LB medium and purified using Endofree MAXI kit (QIAGEN) to obtain the plasmid (581.6 of µg).

Example 2

Establishment of sgp64Tgm

A DNA injection fragment for use in Tgm production was prepared by treating the pCAG-sgp64 vector with the restriction enzymes SalI and PstI, then cutting out the fragment comprising the sgp64 gene (approximately 3.7 kb), collecting the fragment using a Gel Extraction Kit (QIAGEN), and then diluting this fragment to 3 ng/PL using PBS. Mouse pronuclear stage embryos into which the DNA fragment was to be inserted were collected as follows: BALB/cA female mice (Japan Clea) were subjected to superovulation treatment (5 IU of eCG (Serotropin, Teikoku Zoki) was administered intraperitoneally, and 48 hours later, 5 IU of hCG (Puberogen, Sankyo) was administered intraperitoneally), and then mated with male mice of the same strain (Japan Clea). The next morning, the oviducts of female mice found to have a vaginal plug were perfused to collect the pronuclear stage embryos. The DNA fragment was injected into pronuclear stage embryos using a micromanipulator ("Modern Techniques in Gene Targeting" (Yodosha), 190-207, 2000). The following day, embryos that had developed to the two-cell stage were transplanted into the left and right oviducts of one-day pseudopregnant recipient females at ten or so embryos per oviduct (20 or so embryos per individual). Recipient females that did not deliver litters by the expected delivery date were subjected to caesarian section and the pups were nursed by foster parents.

Based on the above methods, the DNA fragment was injected into 497 BALB/cA pronuclear stage mice embryos, and of these the 430 that developed into two-cell stage embryos were transplanted into the oviducts of pseudopregnant recipient females. As a result, 66 pups were obtained. Gene introduction into the obtained pups was confirmed as described below.

The mouse tails were collected and treated at 55° C. overnight with Lysis buffer (50 mM Tris-HCl pH 8.0, 0.1 M NaCl, 20 mM EDTA, 1% SDS, Proteinase K 1 mg/mL; TaKaRa). Genomic DNA was then extracted using an automatic nucleic acid isolation system (KURABO, NA-1000P), and the introduced gene was confirmed by Southern blotting and PCR. Confirmation of the introduced gene by Southern blotting was performed by treating the extracted genomic DNA (15 µg) with the restriction enzyme EcoRI, electrophoresing in an agarose gel, and transferring onto a nylon membrane (Hybond N+; Amersham) by the alkaline blotting method. An approximately 1.5 kb restriction enzyme EcoRI-treated fragment of the pCAG-sgp64 vector comprising sgp64 was used as a probe. This was labeled with $^{32}P$ and Southern blotting was performed by hybridizing it with the blotted genomic DNA. Hybridization was carried out overnight at 45° C. using 5× SSPE, 50% formamide, 5× Denhardt, and 0.5% SDS as the hybridization solution. The nylon membranes were washed in 2× SSC containing 0.1% SDS at 65° C. for 30 minutes, and then in 1× SSC containing 0.1% SDS at 65° C. for 30 minutes. Thereafter, signals were detected using BAS2000 (FUJIX).

Confirmation of the introduced gene by PCR was carried out using the above-mentioned 64F1 as the sense primer, and the above-mentioned s64R1 as the antisense primer, under the following conditions: the composition of the PCR reaction solution was 1 µL of genomic DNA (100 ng/µL), 5 µL of 10× ExTaq buffer (TaKaRa), 4 µL of dNTP mixture comprised in the ExTaq kit, 1 µL of 64F1 primer (10 µmole/L), 1 µL of s64R1 primer (10 µmole/L), 0.5 µL of ExTaq (5 units/µL, TaKaRa), and 37.5 µL of $H_2O$. The reaction was carried out by heating at 94° C. for five minutes, and then performing 35 cycles of 94° C. for 15 seconds, 57° C. for 30 seconds, and 72° C. for 30 seconds; subsequently, the mixture was treated at 72° C. for seven minutes, and then stored at 4° C. The amplified product was subjected to electrophoresis, and the presence or absence of a band of approximately 1.5 kb was verified.

This method confirmed that three of the 66 pups were Tgm carrying the sgp64 gene (hereinafter, Tgm obtained by inserting the DNA fragment will be referred to as "founder mice") (Table 1). One of the three founder mice was male, and the other two were female.

TABLE 1

|  | Number of viable eggs/ number of eggs receiving injection | Number of eggs transplanted | Number of eggs implanted | Number of pups (female, male) | Number of weanlings (female, male) | Founder |
|---|---|---|---|---|---|---|
| 1st | 120/133 | 114 | 61 | 29 (15, 14) | 28 (14, 14) | 0 |
| 2nd | 78/88 | 76 | 22 | 4 (2, 2) | 4 (2, 2) | 0 |
| 3rd | 102/111 | 101 | 55 | 12 (7, 5) | 11 (7, 4) | 1 female, 1 male |
| 4th | 130/165 | 126 | 64 | 21 (11, 10) | 15 (8, 7) | 1 female |
| Total | 430/497 | 417 | 202 | 66 (35, 31) | 58 (31, 27) | 2 females, 1 male |

When eight weeks old, the obtained founder mice were mated with BALB/cA mice. Specifically, of the three founder mice, 26 pups were obtained by mating the male founder mouse (line number 41) with five females, and of these pups, 12 were Tgm (F1 mice). Nine of the 16 pups obtained from the first female founder mouse (line number 36) were Tgm (F1 mice, including males and females), and four of these were males (Table 2). Eight of the 15 pups obtained from the other female founder mouse (line number 51) were Tgm (F1 mice, including males and females), and one of these was a male (Table 2).

TABLE 2

| Line number | Sex | Number of deliveries | Litter size | Number of Tgm (F1) |
|---|---|---|---|---|
| 36 | Female | 2 | 7 females, 9 males | 5 females, 4 males |
| 41 | Male | 5 | 11 females, 15 males | 4 females, 8 males |
| 51 | Female | 2 | 8 females, 7 males | 7 females, 1 male |

Example 3

Fertility of Male Tgm

The fertility of the male Tgm (F1 mice) obtained in Example 2 was examined. Fertility was confirmed by mating eight-week-old male sgp64Tgm (F1 mice) with BALB/cA mice, and confirming the presence and number of pups.

Male Tgm (F1 mice) obtained from each of the three founder lines (one animal from each line) were mated with two females to give nine pups (five females, four males), nine pups (two females, seven males), and ten pups (six females, four males) respectively, and of these, nine pups (five females, four males), eight pups (two females, six males), and five pups (four females, one male) were Tgm (Table 3). The male Tgm in all three lines were confirmed to have normal fertility.

Fertility Results of Male sgp64Tgm (F1 Mice)

TABLE 3

| Line number | Number of deliveries | Litter size | Number of Tgm |
|---|---|---|---|
| 36 | 2 | 5 females, 4 males | 5 females, 4 males |
| 41 | 2 | 2 females, 7 males | 2 females, 6 males |
| 51 | 2 | 6 females, 4 males | 4 females, 1 male |

Example 4

Confirmation of Tolerance to gp64 by Western Blotting

To confirm induction of tolerance to gp64, sgp64Tgm were immunized with a budding baculovirus (pepT1-AcMNPV (pepT1-BV)), as set out below.

Immunization was carried out by producing an emulsion according to standard methods using Freund's complete adjuvant (Difco) and incomplete adjuvant (Difco), and administering it subcutaneously. The first immunizing dose was 1 mg/animal, and the second immunizing dose was 0.5 mg/animal. The second immunization was carried out 14 days after the first. After 17 days from the first immunization, blood was sampled from the orbit, and serum was collected. As controls, non-transgenic mice were immunized similarly, and their sera were collected.

The following Western blot analysis was carried out to confirm tolerance to gp64 in the Tgm:

pepT1-BV used as the antigen was subjected to SDS-PAGE at 1 μg/lane using a 12% gel and under reducing conditions. After electrophoresis, electroblotting onto a PVDF membrane was carried out. The serum collected above was diluted to 1/1000, and reacted with this membrane, which was then washed three times for five minutes at room temperature using PBS-T (PBS containing 0.05% Tween20). After washing, biotin-anti-mouse IgG(γ) (Zymed) diluted to 1/1000, and streptavidin-alkaline phosphatase (Zymed) were reacted with the membrane. Alkaline Phosphatase Staining Kit (Nakalai) was used for staining.

Figure 3:
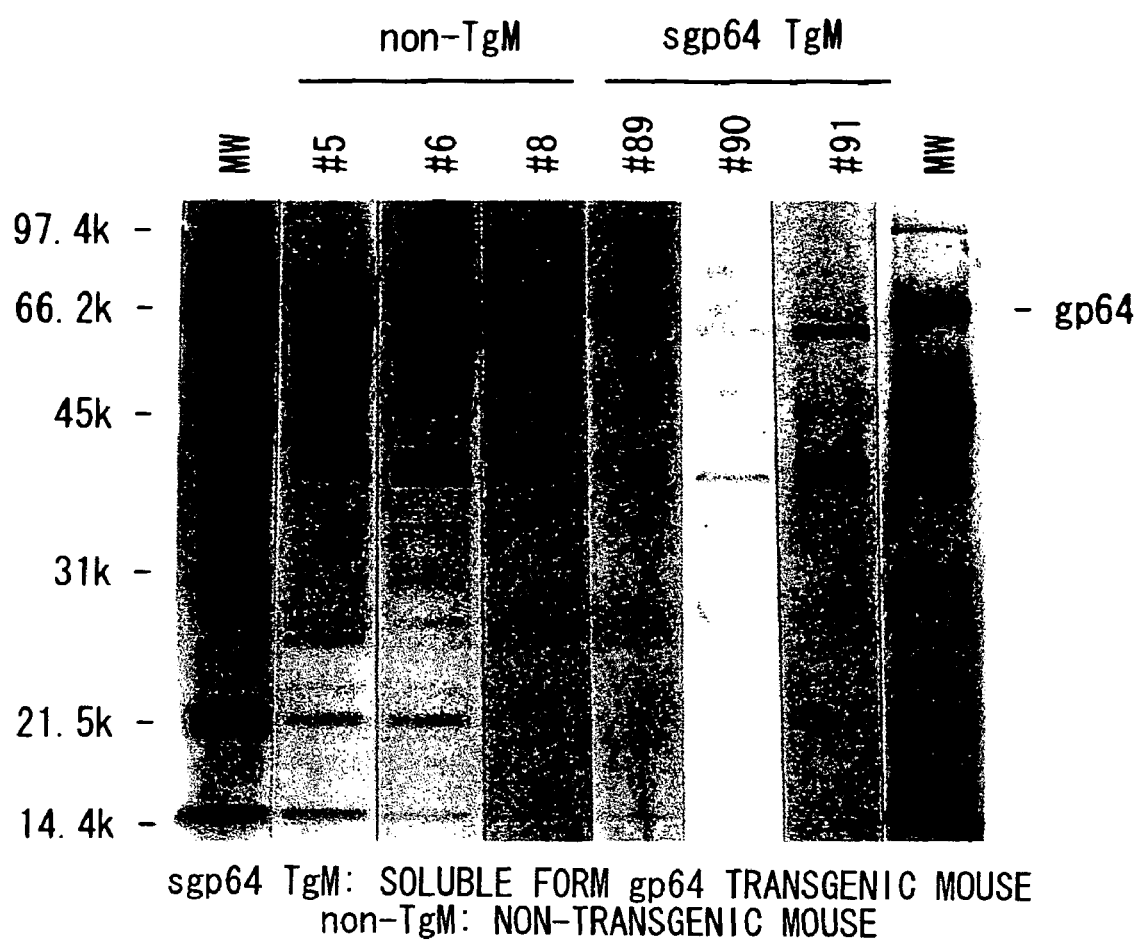
FIG. 3 is a photograph showing a Western blot with anti-mouse IgG to confirm that immunotolerance against gp64 is induced in sgp64Tgm.

In the case of non-transgenic mice (non-Tgm), staining with anti-mouse IgG resulted in strong staining for all three mice (FIG. 3). On the other hand, there was hardly any gp64 staining for the sgp64Tgm, and this confirmed the induction of tolerance to gp64 in sgp64Tgm.

INDUSTRIAL APPLICABILITY

The present invention provided new transgenic animals that overcome the problem of male infertility, which existed in conventional transgenic animals into which the gene for the baculovirus membrane protein gp64 had been introduced. The above-mentioned problem was solved by expressing a soluble gp64 (that is, expressing gp64 outside the cell membrane), which was prepared by methods such as deleting a sequence encoding the transmembrane region from the gene encoding the gp64 membrane protein. Therefore, the emergence of unfavorable phenotypes, such as the unfavorable characteristic of male infertility in transgenic animals into which a gene encoding a full-length membrane protein has been introduced, can be avoided in transgenic animals into which a gene encoding a soluble form of the membrane protein has been introduced, as in the present invention.

As described above, just as for transgenic animals into which genes encoding a full-length membrane protein had been introduced, transgenic animals into which genes encoding a soluble protein had been introduced have been confirmed to have induced immunotolerance to the membrane protein. Therefore, when the immunogens have contaminating membrane proteins as background antigens, it is advantageous to use, as animals to be immunized, the transgenic animals which carry genes encoding soluble proteins that lack a transmembrane region, and such, of these membrane proteins as exogenous genes. That is, since immunotolerance against background antigen membrane proteins is induced, antibodies specific to the desired antigen are produced advantageously, and since unfavorable phenotypes of transgenic animals into which the full-length membrane protein has been introduced can be avoided in these immunized animals, they will be utilized even more readily as systems for antibody production.

The antibodies produced using the animals of the present invention are not contaminated or very slightly contaminated by antibodies against background antigens, and they are therefore provided as highly pure antibodies.

The invention claimed is:

1. A transgenic mouse whose genome comprises a nucleic acid sequence encoding baculovirus gp64, wherein the gp64 is soluble and lacks a transmembrane region, and wherein the mouse is fertile.

2. A method for producing an antibody to a target antigen, the method comprising:

(A) providing a transgenic mouse whose genome comprises a nucleic acid sequence encoding baculovirus gp64, wherein the gp64 is soluble and lacks a transmembrane region, and wherein the mouse is fertile;

(B) providing an immunogen comprising i) a) a baculovirus particle comprising gp64; and b) a target antigen on the surface of the particle; or ii) a) a portion of a baculovirus particle comprising gp64; and b) a target antigen; and (C) immunizing the mouse with the immunogen so that an antibody to the target antigen is produced.

3. The method of claim 2, wherein the immunogen comprises a) a baculovirus particle comprising gp64; and b) a target antigen on the surface of the particle, wherein the target antigen is a protein.

4. The method of claim 3, wherein the target antigen comprises a membrane protein.

5. The method of claim 3, wherein the mouse is male.

6. The method of claim 2, wherein said target antigen comprises a membrane protein.

7. The method of claim 2, wherein the immunogen comprises a) a portion of a baculovirus particle comprising gp64; and b) a target antigen.

8. The method of claim 7, wherein the target antigen comprises a protein.

9. The method of claim 7, wherein the portion of the baculovirus particle also comprises viral envelope.

10. The method of claim 9, wherein the target antigen comprises a membrane protein.

11. The method of claim 7, wherein the target antigen comprises a lipid or a sugar chain.

12. The method of claim 7, wherein the mouse is male.

13. The method of claim 2, wherein the mouse is male.

14. The transgenic mouse of claim 1, wherein the mouse is male.

* * * * *

UNITED STATES PATENT AND TRADEMARK OFFICE
CERTIFICATE OF CORRECTION

PATENT NO. : 7,964,767 B2
APPLICATION NO. : 10/594690
DATED : June 21, 2011
INVENTOR(S) : Tatsuhiko Kodama et al.

It is certified that error appears in the above-identified patent and that said Letters Patent is hereby corrected as shown below:

On the Title Page
Item (56) (Other Publications), line 5:
    delete "acncer" and replace with -- cancer --.

Pg 2, Item (56) (Other Publications), line 63:
    delete "$\alpha_2$-adrenergic" and replace with -- $\beta_2$-adrenergic --.

Pg 2, Item (56) (Other Publications), line 58:
    delete "$\alpha$-lactam" and replace with -- $\beta$-lactam --.

Pg 3, Item (56) (Other Publications), line 2:
    delete "CarcinomasL" and replace with -- Carcinomas: --.

Column 14, line 37:
    delete "ng/PL" and replace with -- ng/µL --.

Column 15, line 10:
    delete "$^{32}$p" and replace with -- $^{32}$P --.

Signed and Sealed this
Eighth Day of November, 2011

David J. Kappos
*Director of the United States Patent and Trademark Office*

SEQUENCE LISTING

<160> NUMBER OF SEQ ID NOS: 10

<210> SEQ ID NO 1
<211> LENGTH: 1539
<212> TYPE: DNA
<213> ORGANISM: Baculovirus
<220> FEATURE:
<221> NAME/KEY: CDS
<222> LOCATION: (1)..(1539)

<400> SEQUENCE: 1

```
atg gta agc gct att gtt tta tat gtg ctt ttg gcg gcg gcg gcg cat      48
Met Val Ser Ala Ile Val Leu Tyr Val Leu Leu Ala Ala Ala Ala His
1               5                   10                  15 tct gcc ttt gcg gcg gag cac tgc aac gcg caa atg aag acg ggt ccg      96
Ser Ala Phe Ala Ala Glu His Cys Asn Ala Gln Met Lys Thr Gly Pro
                20                  25                  30 tac aag att aaa aac ttg gac att acc ccc ccc aag gaa acg ctg caa     144
Tyr Lys Ile Lys Asn Leu Asp Ile Thr Pro Pro Lys Glu Thr Leu Gln
            35                  40                  45 aag gac gtg gaa atc acc atc gtg gag acg gac tac aac gaa aac gtg     192
Lys Asp Val Glu Ile Thr Ile Val Glu Thr Asp Tyr Asn Glu Asn Val
        50                  55                  60 att atc ggc tac aag ggg tac tac cag gcg tat gcg tac aac ggc ggc     240
```

-continued

```
Ile Ile Gly Tyr Lys Gly Tyr Tyr Gln Ala Tyr Ala Tyr Asn Gly Gly
 65                  70                  75                  80 tcg ctg gat ccc aac aca cgc gtc gaa gaa acc atg aaa acg ctg aat    288
Ser Leu Asp Pro Asn Thr Arg Val Glu Glu Thr Met Lys Thr Leu Asn
                 85                  90                  95 gtg ggc aaa gag gat ttg ctt atg tgg agc atc agg cag cag tgc gag    336
Val Gly Lys Glu Asp Leu Leu Met Trp Ser Ile Arg Gln Gln Cys Glu
            100                 105                 110 gtg ggc gaa gag ctg atc gac cgt tgg ggc agt gac agc gac gac tgt    384
Val Gly Glu Glu Leu Ile Asp Arg Trp Gly Ser Asp Ser Asp Asp Cys
        115                 120                 125 ttt cgc gac aac gag ggc cgc ggc cag tgg gtc aaa ggc aaa gag ttg    432
Phe Arg Asp Asn Glu Gly Arg Gly Gln Trp Val Lys Gly Lys Glu Leu
    130                 135                 140 gtg aag cgg cag aat aac aat cac ttt gcg cac cac acg tgc aac aaa    480
Val Lys Arg Gln Asn Asn Asn His Phe Ala His His Thr Cys Asn Lys
145                 150                 155                 160 tcg tgg cga tgc ggc att tcc act tcg aaa atg tac agc agg ctc gag    528
Ser Trp Arg Cys Gly Ile Ser Thr Ser Lys Met Tyr Ser Arg Leu Glu
                165                 170                 175 tgc cag gac gac acg gac gag tgc cag gta tac att ttg gac gct gag    576
Cys Gln Asp Asp Thr Asp Glu Cys Gln Val Tyr Ile Leu Asp Ala Glu
            180                 185                 190 ggc aac ccc atc aac gtg acc gtg gac act gtg ctt cat cga gac ggc    624
Gly Asn Pro Ile Asn Val Thr Val Asp Thr Val Leu His Arg Asp Gly
        195                 200                 205 gtg agt atg att ctc aaa caa aag tct acg ttc acc acg cgc caa ata    672
Val Ser Met Ile Leu Lys Gln Lys Ser Thr Phe Thr Thr Arg Gln Ile
    210                 215                 220 aaa gct gcg tgt ctg ctc att aaa gat gac aaa aat aac ccc gag tcg    720
Lys Ala Ala Cys Leu Leu Ile Lys Asp Asp Lys Asn Asn Pro Glu Ser
225                 230                 235                 240 gtg aca cgc gaa cac tgt ttg att gac aat gat ata tat gat ctt tct    768
Val Thr Arg Glu His Cys Leu Ile Asp Asn Asp Ile Tyr Asp Leu Ser
                245                 250                 255 aaa aac acg tgg aac tgc aag ttt aac aga tgc att aaa cgc aaa gtc    816
Lys Asn Thr Trp Asn Cys Lys Phe Asn Arg Cys Ile Lys Arg Lys Val
            260                 265                 270 gag cac cga gtc aag aag cgg ccg ccc act tgg cgc cac aac gtt aga    864
Glu His Arg Val Lys Lys Arg Pro Pro Thr Trp Arg His Asn Val Arg
        275                 280                 285 gcc aag tac aca gag gga gac act gcc acc aaa ggc gac ctg atg cat    912
Ala Lys Tyr Thr Glu Gly Asp Thr Ala Thr Lys Gly Asp Leu Met His
    290                 295                 300 att caa gag gag ctg atg tac gaa aac gat ttg ctg aaa atg aac att    960
Ile Gln Glu Glu Leu Met Tyr Glu Asn Asp Leu Leu Lys Met Asn Ile
305                 310                 315                 320 gag ctg atg cat gcg cac atc aac aag cta aac aat atg ctg cac gac    1008
Glu Leu Met His Ala His Ile Asn Lys Leu Asn Asn Met Leu His Asp
                325                 330                 335 ctg ata gtc tcc gtg gcc aag gtg gac gag cgt ttg att ggc aat ctc    1056
Leu Ile Val Ser Val Ala Lys Val Asp Glu Arg Leu Ile Gly Asn Leu
            340                 345                 350 atg aac aac tct gtt tct tca aca ttt ttg tcg gac gac acg ttt ttg    1104
Met Asn Asn Ser Val Ser Ser Thr Phe Leu Ser Asp Asp Thr Phe Leu
        355                 360                 365 ctg atg ccg tgc acc aat ccg ccg gca cac acc agt aat tgc tac aac    1152
Leu Met Pro Cys Thr Asn Pro Pro Ala His Thr Ser Asn Cys Tyr Asn
    370                 375                 380 aac agc atc tac aaa gaa ggg cgt tgg gtg gcc aac acg gac tcg tcg    1200
```

```
Asn Ser Ile Tyr Lys Glu Gly Arg Trp Val Ala Asn Thr Asp Ser Ser
385                 390                 395                 400 caa tgc ata gat ttt agc aac tac aag gaa cta gca att gac gac gac     1248
Gln Cys Ile Asp Phe Ser Asn Tyr Lys Glu Leu Ala Ile Asp Asp Asp
            405                 410                 415 gtc gag ttt tgg atc ccg acc atc ggc aac acg acc tat cac gac agt     1296
Val Glu Phe Trp Ile Pro Thr Ile Gly Asn Thr Thr Tyr His Asp Ser
        420                 425                 430 tgg aaa gat gcc agc ggc tgg tcg ttt att gcc caa caa aaa agc aac     1344
Trp Lys Asp Ala Ser Gly Trp Ser Phe Ile Ala Gln Gln Lys Ser Asn
            435                 440                 445 ctc ata acc acc atg gag aac acc aag ttt ggc ggc gtc ggc acc agt     1392
Leu Ile Thr Thr Met Glu Asn Thr Lys Phe Gly Gly Val Gly Thr Ser
        450                 455                 460 ctg agc gac atc act tcc atg gct gaa ggc gaa ttg gcc gct aaa ttg     1440
Leu Ser Asp Ile Thr Ser Met Ala Glu Gly Glu Leu Ala Ala Lys Leu
465                 470                 475                 480 act tcg ttc atg ttt ggt cat gta gtt aac ttt gta att ata tta att     1488
Thr Ser Phe Met Phe Gly His Val Val Asn Phe Val Ile Ile Leu Ile
            485                 490                 495 gtg att tta ttt ttg tac tgt atg att aga aac cgt aat aga caa tat     1536
Val Ile Leu Phe Leu Tyr Cys Met Ile Arg Asn Arg Asn Arg Gln Tyr
        500                 505                 510 taa                                                                  1539

<210> SEQ ID NO 2
<211> LENGTH: 512
<212> TYPE: PRT
<213> ORGANISM: Baculovirus

<400> SEQUENCE: 2

Met Val Ser Ala Ile Val Leu Tyr Val Leu Leu Ala Ala Ala Ala His
1               5                   10                  15

Ser Ala Phe Ala Ala Glu His Cys Asn Ala Gln Met Lys Thr Gly Pro
            20                  25                  30

Tyr Lys Ile Lys Asn Leu Asp Ile Thr Pro Pro Lys Glu Thr Leu Gln
        35                  40                  45

Lys Asp Val Glu Ile Thr Ile Val Glu Thr Asp Tyr Asn Glu Asn Val
    50                  55                  60

Ile Ile Gly Tyr Lys Gly Tyr Tyr Gln Ala Tyr Ala Tyr Asn Gly Gly
65                  70                  75                  80

Ser Leu Asp Pro Asn Thr Arg Val Glu Glu Thr Met Lys Thr Leu Asn
            85                  90                  95

Val Gly Lys Glu Asp Leu Leu Met Trp Ser Ile Arg Gln Gln Cys Glu
        100                 105                 110

Val Gly Glu Glu Leu Ile Asp Arg Trp Gly Ser Asp Ser Asp Asp Cys
    115                 120                 125

Phe Arg Asp Asn Glu Gly Arg Gly Gln Trp Val Lys Gly Lys Glu Leu
    130                 135                 140

Val Lys Arg Gln Asn Asn Asn His Phe Ala His His Thr Cys Asn Lys
145                 150                 155                 160

Ser Trp Arg Cys Gly Ile Ser Thr Ser Lys Met Tyr Ser Arg Leu Glu
            165                 170                 175

Cys Gln Asp Asp Thr Asp Glu Cys Gln Val Tyr Ile Leu Asp Ala Glu
        180                 185                 190

Gly Asn Pro Ile Asn Val Thr Val Asp Thr Val Leu His Arg Asp Gly
    195                 200                 205
```

```
Val Ser Met Ile Leu Lys Gln Lys Ser Thr Phe Thr Thr Arg Gln Ile
        210                 215                 220

Lys Ala Ala Cys Leu Leu Ile Lys Asp Asp Lys Asn Asn Pro Glu Ser
225                 230                 235                 240

Val Thr Arg Glu His Cys Leu Ile Asp Asn Asp Ile Tyr Asp Leu Ser
                245                 250                 255

Lys Asn Thr Trp Asn Cys Lys Phe Asn Arg Cys Ile Lys Arg Lys Val
            260                 265                 270

Glu His Arg Val Lys Lys Arg Pro Pro Thr Trp Arg His Asn Val Arg
        275                 280                 285

Ala Lys Tyr Thr Glu Gly Asp Thr Ala Thr Lys Gly Asp Leu Met His
290                 295                 300

Ile Gln Glu Glu Leu Met Tyr Glu Asn Asp Leu Leu Lys Met Asn Ile
305                 310                 315                 320

Glu Leu Met His Ala His Ile Asn Lys Leu Asn Asn Met Leu His Asp
                325                 330                 335

Leu Ile Val Ser Val Ala Lys Val Asp Glu Arg Leu Ile Gly Asn Leu
            340                 345                 350

Met Asn Asn Ser Val Ser Ser Thr Phe Leu Ser Asp Asp Thr Phe Leu
        355                 360                 365

Leu Met Pro Cys Thr Asn Pro Pro Ala His Thr Ser Asn Cys Tyr Asn
370                 375                 380

Asn Ser Ile Tyr Lys Glu Gly Arg Trp Val Ala Asn Thr Asp Ser Ser
385                 390                 395                 400

Gln Cys Ile Asp Phe Ser Asn Tyr Lys Glu Leu Ala Ile Asp Asp Asp
                405                 410                 415

Val Glu Phe Trp Ile Pro Thr Ile Gly Asn Thr Thr Tyr His Asp Ser
            420                 425                 430

Trp Lys Asp Ala Ser Gly Trp Ser Phe Ile Ala Gln Gln Lys Ser Asn
        435                 440                 445

Leu Ile Thr Thr Met Glu Asn Thr Lys Phe Gly Gly Val Gly Thr Ser
450                 455                 460

Leu Ser Asp Ile Thr Ser Met Ala Glu Gly Leu Ala Ala Lys Leu
465                 470                 475                 480

Thr Ser Phe Met Phe Gly His Val Val Asn Phe Val Ile Ile Leu Ile
                485                 490                 495

Val Ile Leu Phe Leu Tyr Cys Met Ile Arg Asn Arg Asn Arg Gln Tyr
            500                 505                 510
```

<210> SEQ ID NO 3
<211> LENGTH: 1464
<212> TYPE: DNA
<213> ORGANISM: Baculovirus
<220> FEATURE:
<221> NAME/KEY: CDS
<222> LOCATION: (1)..(1464)

<400> SEQUENCE: 3

```
atg gta agc gct att gtt tta tat gtg ctt ttg gcg gcg gcg gcg cat      48
Met Val Ser Ala Ile Val Leu Tyr Val Leu Leu Ala Ala Ala Ala His
1               5                   10                  15 tct gcc ttt gcg gcg gag cac tgc aac gcg caa atg aag acg ggt ccg      96
Ser Ala Phe Ala Ala Glu His Cys Asn Ala Gln Met Lys Thr Gly Pro
                20                  25                  30 tac aag att aaa aac ttg gac att acc ccg ccc aag gaa acg ctg caa     144
Tyr Lys Ile Lys Asn Leu Asp Ile Thr Pro Pro Lys Glu Thr Leu Gln
            35                  40                  45
```

```
aag gac gtg gaa atc acc atc gtg gag acg gac tac aac gaa aac gtg      192
Lys Asp Val Glu Ile Thr Ile Val Glu Thr Asp Tyr Asn Glu Asn Val
 50                  55                  60 att atc ggc tac aag ggg tac tac cag gcg tat gcg tac aac ggc ggc      240
Ile Ile Gly Tyr Lys Gly Tyr Tyr Gln Ala Tyr Ala Tyr Asn Gly Gly
 65                  70                  75                  80 tcg ctg gat ccc aac aca cgc gtc gaa gaa acc atg aaa acg ctg aat      288
Ser Leu Asp Pro Asn Thr Arg Val Glu Glu Thr Met Lys Thr Leu Asn
                 85                  90                  95 gtg ggc aaa gag gat ttg ctt atg tgg agc atc agg cag cag tgc gag      336
Val Gly Lys Glu Asp Leu Leu Met Trp Ser Ile Arg Gln Gln Cys Glu
            100                 105                 110 gtg ggc gaa gag ctg atc gac cgt tgg ggc agt gac agc gac gac tgt      384
Val Gly Glu Glu Leu Ile Asp Arg Trp Gly Ser Asp Ser Asp Asp Cys
            115                 120                 125 ttt cgc gac aac gag ggc cgc ggc cag tgg gtc aaa ggc aaa gag ttg      432
Phe Arg Asp Asn Glu Gly Arg Gly Gln Trp Val Lys Gly Lys Glu Leu
130                 135                 140 gtg aag cgg cag aat aac aat cac ttt gcg cac cac acg tgc aac aaa      480
Val Lys Arg Gln Asn Asn Asn His Phe Ala His His Thr Cys Asn Lys
145                 150                 155                 160 tcg tgg cga tgc ggc att tcc act tcg aaa atg tac agc agg ctc gag      528
Ser Trp Arg Cys Gly Ile Ser Thr Ser Lys Met Tyr Ser Arg Leu Glu
                165                 170                 175 tgc cag gac gac acg gac gag tgc cag gta tac att ttg gac gct gag      576
Cys Gln Asp Asp Thr Asp Glu Cys Gln Val Tyr Ile Leu Asp Ala Glu
            180                 185                 190 ggc aac ccc atc aac gtg acc gtg gac act gtg ctt cat cga gac ggc      624
Gly Asn Pro Ile Asn Val Thr Val Asp Thr Val Leu His Arg Asp Gly
            195                 200                 205 gtg agt atg att ctc aaa caa aag tct acg ttc acc acg cgc caa ata      672
Val Ser Met Ile Leu Lys Gln Lys Ser Thr Phe Thr Thr Arg Gln Ile
210                 215                 220 aaa gct gcg tgt ctg ctc att aaa gat gac aaa aat aac ccc gag tcg      720
Lys Ala Ala Cys Leu Leu Ile Lys Asp Asp Lys Asn Asn Pro Glu Ser
225                 230                 235                 240 gtg aca cgc gaa cac tgt ttg att gac aat gat ata tat gat ctt tct      768
Val Thr Arg Glu His Cys Leu Ile Asp Asn Asp Ile Tyr Asp Leu Ser
                245                 250                 255 aaa aac acg tgg aac tgc aag ttt aac aga tgc att aaa cgc aaa gtc      816
Lys Asn Thr Trp Asn Cys Lys Phe Asn Arg Cys Ile Lys Arg Lys Val
            260                 265                 270 gag cac cga gtc aag aag cgg ccg ccc act tgg cgc cac aac gtt aga      864
Glu His Arg Val Lys Lys Arg Pro Pro Thr Trp Arg His Asn Val Arg
            275                 280                 285 gcc aag tac aca gag gga gac act gcc acc aaa ggc gac ctg atg cat      912
Ala Lys Tyr Thr Glu Gly Asp Thr Ala Thr Lys Gly Asp Leu Met His
290                 295                 300 att caa gag gag ctg atg tac gaa aac gat ttg ctg aaa atg aac att      960
Ile Gln Glu Glu Leu Met Tyr Glu Asn Asp Leu Leu Lys Met Asn Ile
305                 310                 315                 320 gag ctg atg cat gcg cac atc aac aag cta aac aat atg ctg cac gac     1008
Glu Leu Met His Ala His Ile Asn Lys Leu Asn Asn Met Leu His Asp
                325                 330                 335 ctg ata gtc tcc gtg gcc aag gtg gac gag cgt ttg att ggc aat ctc     1056
Leu Ile Val Ser Val Ala Lys Val Asp Glu Arg Leu Ile Gly Asn Leu
            340                 345                 350 atg aac aac tct gtt tct tca aca ttt ttg tcg gac gac acg ttt ttg     1104
Met Asn Asn Ser Val Ser Ser Thr Phe Leu Ser Asp Asp Thr Phe Leu
            355                 360                 365
```

```
ctg atg ccg tgc acc aat ccg ccg gca cac acc agt aat tgc tac aac    1152
Leu Met Pro Cys Thr Asn Pro Pro Ala His Thr Ser Asn Cys Tyr Asn
    370             375                 380 aac agc atc tac aaa gaa ggg cgt tgg gtg gcc aac acg gac tcg tcg    1200
Asn Ser Ile Tyr Lys Glu Gly Arg Trp Val Ala Asn Thr Asp Ser Ser
385             390                 395                 400 caa tgc ata gat ttt agc aac tac aag gaa cta gca att gac gac gac    1248
Gln Cys Ile Asp Phe Ser Asn Tyr Lys Glu Leu Ala Ile Asp Asp Asp
                405                 410                 415 gtc gag ttt tgg atc ccg acc atc ggc aac acg acc tat cac gac agt    1296
Val Glu Phe Trp Ile Pro Thr Ile Gly Asn Thr Thr Tyr His Asp Ser
            420                 425                 430 tgg aaa gat gcc agc ggc tgg tcg ttt att gcc caa caa aaa agc aac    1344
Trp Lys Asp Ala Ser Gly Trp Ser Phe Ile Ala Gln Gln Lys Ser Asn
        435                 440                 445 ctc ata acc acc atg gag aac acc aag ttt ggc ggc gtc ggc acc agt    1392
Leu Ile Thr Thr Met Glu Asn Thr Lys Phe Gly Gly Val Gly Thr Ser
    450                 455                 460 ctg agc gac atc act tcc atg gct gaa ggc gaa ttg gcc gct aaa ttg    1440
Leu Ser Asp Ile Thr Ser Met Ala Glu Gly Glu Leu Ala Ala Lys Leu
465                 470                 475                 480 act tcg ttc atg ttt ggt cat gta                                    1464
Thr Ser Phe Met Phe Gly His Val
                485
```

<210> SEQ ID NO 4
<211> LENGTH: 488
<212> TYPE: PRT
<213> ORGANISM: Baculovirus

<400> SEQUENCE: 4

```
Met Val Ser Ala Ile Val Leu Tyr Val Leu Ala Ala Ala His
1               5                   10                  15

Ser Ala Phe Ala Ala Glu His Cys Asn Ala Gln Met Lys Thr Gly Pro
            20                  25                  30

Tyr Lys Ile Lys Asn Leu Asp Ile Thr Pro Pro Lys Glu Thr Leu Gln
        35                  40                  45

Lys Asp Val Glu Ile Thr Ile Val Glu Thr Asp Tyr Asn Glu Asn Val
    50                  55                  60

Ile Ile Gly Tyr Lys Gly Tyr Tyr Gln Ala Tyr Ala Tyr Asn Gly Gly
65                  70                  75                  80

Ser Leu Asp Pro Asn Thr Arg Val Glu Glu Thr Met Lys Thr Leu Asn
                85                  90                  95

Val Gly Lys Glu Asp Leu Leu Met Trp Ser Ile Arg Gln Gln Cys Glu
            100                 105                 110

Val Gly Glu Glu Leu Ile Asp Arg Trp Gly Ser Asp Ser Asp Asp Cys
        115                 120                 125

Phe Arg Asp Asn Glu Gly Arg Gly Gln Trp Val Lys Gly Lys Glu Leu
    130                 135                 140

Val Lys Arg Gln Asn Asn Asn His Phe Ala His His Thr Cys Asn Lys
145                 150                 155                 160

Ser Trp Arg Cys Gly Ile Ser Thr Ser Lys Met Tyr Ser Arg Leu Glu
                165                 170                 175

Cys Gln Asp Asp Thr Asp Glu Cys Gln Val Tyr Ile Leu Asp Ala Glu
            180                 185                 190

Gly Asn Pro Ile Asn Val Thr Val Asp Thr Val Leu His Arg Asp Gly
        195                 200                 205

Val Ser Met Ile Leu Lys Gln Lys Ser Thr Phe Thr Thr Arg Gln Ile
```

```
            210                 215                 220
Lys Ala Ala Cys Leu Leu Ile Lys Asp Asp Lys Asn Asn Pro Glu Ser
225                 230                 235                 240

Val Thr Arg Glu His Cys Leu Ile Asp Asn Asp Ile Tyr Asp Leu Ser
                245                 250                 255

Lys Asn Thr Trp Asn Cys Lys Phe Asn Arg Cys Ile Lys Arg Lys Val
            260                 265                 270

Glu His Arg Val Lys Lys Arg Pro Pro Thr Trp Arg His Asn Val Arg
        275                 280                 285

Ala Lys Tyr Thr Glu Gly Asp Thr Ala Thr Lys Gly Asp Leu Met His
    290                 295                 300

Ile Gln Glu Glu Leu Met Tyr Glu Asn Asp Leu Leu Lys Met Asn Ile
305                 310                 315                 320

Glu Leu Met His Ala His Ile Asn Lys Leu Asn Asn Met Leu His Asp
                325                 330                 335

Leu Ile Val Ser Val Ala Lys Val Asp Glu Arg Leu Ile Gly Asn Leu
            340                 345                 350

Met Asn Asn Ser Val Ser Ser Thr Phe Leu Ser Asp Asp Thr Phe Leu
        355                 360                 365

Leu Met Pro Cys Thr Asn Pro Pro Ala His Thr Ser Asn Cys Tyr Asn
    370                 375                 380

Asn Ser Ile Tyr Lys Glu Gly Arg Trp Val Ala Asn Thr Asp Ser Ser
385                 390                 395                 400

Gln Cys Ile Asp Phe Ser Asn Tyr Lys Glu Leu Ala Ile Asp Asp
                405                 410                 415

Val Glu Phe Trp Ile Pro Thr Ile Gly Asn Thr Thr Tyr His Asp Ser
            420                 425                 430

Trp Lys Asp Ala Ser Gly Trp Ser Phe Ile Ala Gln Gln Lys Ser Asn
        435                 440                 445

Leu Ile Thr Thr Met Glu Asn Thr Lys Phe Gly Gly Val Gly Thr Ser
    450                 455                 460

Leu Ser Asp Ile Thr Ser Met Ala Glu Gly Glu Leu Ala Ala Lys Leu
465                 470                 475                 480

Thr Ser Phe Met Phe Gly His Val
                485
```

<210> SEQ ID NO 5
<211> LENGTH: 28
<212> TYPE: DNA
<213> ORGANISM: Artificial
<220> FEATURE:
<223> OTHER INFORMATION: an artificially synthesized primer sequence

<400> SEQUENCE: 5
gaattccacc atggtaagcg ctattgtt        28

<210> SEQ ID NO 6
<211> LENGTH: 33
<212> TYPE: DNA
<213> ORGANISM: Artificial
<220> FEATURE:
<223> OTHER INFORMATION: an artificially synthesized primer sequence

<400> SEQUENCE: 6
gaattctcat tatacatgac caaacatgaa cga        33

<210> SEQ ID NO 7
<211> LENGTH: 17

-continued

```
<212> TYPE: DNA
<213> ORGANISM: Artificial
<220> FEATURE:
<223> OTHER INFORMATION: an artificially synthesized primer sequence

<400> SEQUENCE: 7
taatacgact cactata                                                    17

<210> SEQ ID NO 8
<211> LENGTH: 24
<212> TYPE: DNA
<213> ORGANISM: Artificial
<220> FEATURE:
<223> OTHER INFORMATION: an artificially synthesized primer sequence

<400> SEQUENCE: 8
catacgattt aggtgacact atag                                            24

<210> SEQ ID NO 9
<211> LENGTH: 1486
<212> TYPE: DNA
<213> ORGANISM: Baculovirus
<220> FEATURE:
<221> NAME/KEY: CDS
<222> LOCATION: (2)..(1474)

<400> SEQUENCE: 9 g aat tcc acc atg gta agc gct att gtt tta tat gtg ctt ttg gcg gcg     49
  Asn Ser Thr Met Val Ser Ala Ile Val Leu Tyr Val Leu Leu Ala Ala
    1               5                  10                  15 gcg gcg cat tct gcc ttt gcg gcg gag cac tgc aac gcg caa atg aag       97
Ala Ala His Ser Ala Phe Ala Ala Glu His Cys Asn Ala Gln Met Lys
                20                  25                  30 acg ggt ccg tac aag att aaa aac ttg gac att acc ccg ccc aag gaa      145
Thr Gly Pro Tyr Lys Ile Lys Asn Leu Asp Ile Thr Pro Pro Lys Glu
            35                  40                  45 acg ctg caa aag gac gtg gaa atc acc atc gtg gag acg gac tac aac      193
Thr Leu Gln Lys Asp Val Glu Ile Thr Ile Val Glu Thr Asp Tyr Asn
        50                  55                  60 gaa aac gtg att atc ggc tac aag ggg tac tac cag gcg tat gcg tac      241
Glu Asn Val Ile Ile Gly Tyr Lys Gly Tyr Tyr Gln Ala Tyr Ala Tyr
65                  70                  75                  80 aac ggc ggc tcg ctg gat ccc aac aca cgc gtc gaa gaa acc atg aaa      289
Asn Gly Gly Ser Leu Asp Pro Asn Thr Arg Val Glu Glu Thr Met Lys
                85                  90                  95 acg ctg aat gtg ggc aaa gag gat ttg ctt atg tgg agc atc agg cag      337
Thr Leu Asn Val Gly Lys Glu Asp Leu Leu Met Trp Ser Ile Arg Gln
            100                 105                 110 cag tgc gag gtg ggc gaa gag ctg atc gac cgt tgg ggc agt gac agc      385
Gln Cys Glu Val Gly Glu Glu Leu Ile Asp Arg Trp Gly Ser Asp Ser
        115                 120                 125 gac gac tgt ttt cgc gac aac gag ggc cgc ggc cag tgg gtc aaa ggc      433
Asp Asp Cys Phe Arg Asp Asn Glu Gly Arg Gly Gln Trp Val Lys Gly
    130                 135                 140 aaa gag ttg gtg aag cgg cag aat aac aat cac ttt gcg cac cac acg      481
Lys Glu Leu Val Lys Arg Gln Asn Asn Asn His Phe Ala His His Thr
145                 150                 155                 160 tgc aac aaa tcg tgg cga tgc ggc att tcc act tcg aaa atg tac agc      529
Cys Asn Lys Ser Trp Arg Cys Gly Ile Ser Thr Ser Lys Met Tyr Ser
                165                 170                 175 agg ctc gag tgc cag gac gac acg gac gag tgc cag gta tac att ttg      577
Arg Leu Glu Cys Gln Asp Asp Thr Asp Glu Cys Gln Val Tyr Ile Leu
            180                 185                 190
```

```
gac gct gag ggc aac ccc atc aac gtg acc gtg gac act gtg ctt cat        625
Asp Ala Glu Gly Asn Pro Ile Asn Val Thr Val Asp Thr Val Leu His
        195                 200                 205 cga gac ggc gtg agt atg att ctc aaa caa aag tct acg ttc acc acg        673
Arg Asp Gly Val Ser Met Ile Leu Lys Gln Lys Ser Thr Phe Thr Thr
    210                 215                 220 cgc caa ata aaa gct gcg tgt ctg ctc att aaa gat gac aaa aat aac        721
Arg Gln Ile Lys Ala Ala Cys Leu Leu Ile Lys Asp Asp Lys Asn Asn
225                 230                 235                 240 ccc gag tcg gtg aca cgc gaa cac tgt ttg att gac aat gat ata tat        769
Pro Glu Ser Val Thr Arg Glu His Cys Leu Ile Asp Asn Asp Ile Tyr
                245                 250                 255 gat ctt tct aaa aac acg tgg aac tgc aag ttt aac aga tgc att aaa        817
Asp Leu Ser Lys Asn Thr Trp Asn Cys Lys Phe Asn Arg Cys Ile Lys
            260                 265                 270 cgc aaa gtc gag cac cga gtc aag aag cgg ccg ccc act tgg cgc cac        865
Arg Lys Val Glu His Arg Val Lys Lys Arg Pro Pro Thr Trp Arg His
        275                 280                 285 aac gtt aga gcc aag tac aca gag gga gac act gcc acc aaa ggc gac        913
Asn Val Arg Ala Lys Tyr Thr Glu Gly Asp Thr Ala Thr Lys Gly Asp
    290                 295                 300 ctg atg cat att caa gag gag ctg atg tac gaa aac gat ttg ctg aaa        961
Leu Met His Ile Gln Glu Glu Leu Met Tyr Glu Asn Asp Leu Leu Lys
305                 310                 315                 320 atg aac att gag ctg atg cat gcg cac atc aac aag cta aac aat atg       1009
Met Asn Ile Glu Leu Met His Ala His Ile Asn Lys Leu Asn Asn Met
                325                 330                 335 ctg cac gac ctg ata gtc tcc gtg gcc aag gtg gac gag cgt ttg att       1057
Leu His Asp Leu Ile Val Ser Val Ala Lys Val Asp Glu Arg Leu Ile
            340                 345                 350 ggc aat ctc atg aac aac tct gtt tct tca aca ttt ttg tcg gac gac       1105
Gly Asn Leu Met Asn Asn Ser Val Ser Ser Thr Phe Leu Ser Asp Asp
        355                 360                 365 acg ttt ttg ctg atg ccg tgc acc aat ccg ccg gca cac acc agt aat       1153
Thr Phe Leu Leu Met Pro Cys Thr Asn Pro Pro Ala His Thr Ser Asn
    370                 375                 380 tgc tac aac aac agc atc tac aaa gaa ggg cgt tgg gtg gcc aac acg       1201
Cys Tyr Asn Asn Ser Ile Tyr Lys Glu Gly Arg Trp Val Ala Asn Thr
385                 390                 395                 400 gac tcg tcg caa tgc ata gat ttt agc aac tac aag gaa cta gca att       1249
Asp Ser Ser Gln Cys Ile Asp Phe Ser Asn Tyr Lys Glu Leu Ala Ile
                405                 410                 415 gac gac gac gtc gag ttt tgg atc ccg acc atc ggc aac acg acc tat       1297
Asp Asp Asp Val Glu Phe Trp Ile Pro Thr Ile Gly Asn Thr Thr Tyr
            420                 425                 430 cac gac agt tgg aaa gat gcc agc ggc tgg tcg ttt att gcc caa caa       1345
His Asp Ser Trp Lys Asp Ala Ser Gly Trp Ser Phe Ile Ala Gln Gln
        435                 440                 445 aaa agc aac ctc ata acc acc atg gag aac acc aag ttt ggc ggc gtc       1393
Lys Ser Asn Leu Ile Thr Thr Met Glu Asn Thr Lys Phe Gly Gly Val
    450                 455                 460 ggc acc agt ctg agc gac atc act tcc atg gct gaa ggc gaa ttg gcc       1441
Gly Thr Ser Leu Ser Asp Ile Thr Ser Met Ala Glu Gly Glu Leu Ala
465                 470                 475                 480 gct aaa ttg act tcg ttc atg ttt ggt cat gta taatgagaat tc             1486
Ala Lys Leu Thr Ser Phe Met Phe Gly His Val
                485                 490

<210> SEQ ID NO 10
<211> LENGTH: 491
<212> TYPE: PRT
```

<213> ORGANISM: Baculovirus

<400> SEQUENCE: 10

Asn Ser Thr Met Val Ser Ala Ile Val Leu Tyr Val Leu Leu Ala Ala
1               5                   10                  15

Ala Ala His Ser Ala Phe Ala Ala Glu His Cys Asn Ala Gln Met Lys
            20                  25                  30

Thr Gly Pro Tyr Lys Ile Lys Asn Leu Asp Ile Thr Pro Pro Lys Glu
        35                  40                  45

Thr Leu Gln Lys Asp Val Glu Ile Thr Ile Val Glu Thr Asp Tyr Asn
50                  55                  60

Glu Asn Val Ile Ile Gly Tyr Lys Gly Tyr Tyr Gln Ala Tyr Ala Tyr
65                  70                  75                  80

Asn Gly Gly Ser Leu Asp Pro Asn Thr Arg Val Glu Glu Thr Met Lys
                85                  90                  95

Thr Leu Asn Val Gly Lys Glu Asp Leu Leu Met Trp Ser Ile Arg Gln
            100                 105                 110

Gln Cys Glu Val Gly Glu Leu Ile Asp Arg Trp Gly Ser Asp Ser
        115                 120                 125

Asp Asp Cys Phe Arg Asp Asn Glu Gly Arg Gly Gln Trp Val Lys Gly
130                 135                 140

Lys Glu Leu Val Lys Arg Gln Asn Asn Asn His Phe Ala His His Thr
145                 150                 155                 160

Cys Asn Lys Ser Trp Arg Cys Gly Ile Ser Thr Ser Lys Met Tyr Ser
                165                 170                 175

Arg Leu Glu Cys Gln Asp Asp Thr Asp Glu Cys Gln Val Tyr Ile Leu
            180                 185                 190

Asp Ala Glu Gly Asn Pro Ile Asn Val Thr Val Asp Thr Val Leu His
        195                 200                 205

Arg Asp Gly Val Ser Met Ile Leu Lys Gln Lys Ser Thr Phe Thr Thr
210                 215                 220

Arg Gln Ile Lys Ala Ala Cys Leu Leu Ile Lys Asp Asp Lys Asn Asn
225                 230                 235                 240

Pro Glu Ser Val Thr Arg Glu His Cys Leu Ile Asp Asn Asp Ile Tyr
                245                 250                 255

Asp Leu Ser Lys Asn Thr Trp Asn Cys Lys Phe Asn Arg Cys Ile Lys
            260                 265                 270

Arg Lys Val Glu His Arg Val Lys Lys Arg Pro Thr Trp Arg His
        275                 280                 285

Asn Val Arg Ala Lys Tyr Thr Glu Gly Asp Thr Ala Thr Lys Gly Asp
290                 295                 300

Leu Met His Ile Gln Glu Glu Leu Met Tyr Glu Asn Asp Leu Leu Lys
305                 310                 315                 320

Met Asn Ile Glu Leu Met His Ala His Ile Asn Lys Leu Asn Asn Met
                325                 330                 335

Leu His Asp Leu Ile Val Ser Val Ala Lys Val Asp Glu Arg Leu Ile
            340                 345                 350

Gly Asn Leu Met Asn Asn Ser Val Ser Ser Thr Phe Leu Ser Asp Asp
        355                 360                 365

Thr Phe Leu Leu Met Pro Cys Thr Asn Pro Ala His Thr Ser Asn
370                 375                 380

Cys Tyr Asn Asn Ser Ile Tyr Lys Glu Gly Arg Trp Val Ala Asn Thr
385                 390                 395                 400

Asp Ser Ser Gln Cys Ile Asp Phe Ser Asn Tyr Lys Glu Leu Ala Ile

```
                       405                    410                     415

Asp Asp Asp Val Glu Phe Trp Ile Pro Thr Ile Gly Asn Thr Thr Tyr
                420                 425                 430

His Asp Ser Trp Lys Asp Ala Ser Gly Trp Ser Phe Ile Ala Gln Gln
            435                 440                 445

Lys Ser Asn Leu Ile Thr Thr Met Glu Asn Thr Lys Phe Gly Gly Val
        450                 455                 460

Gly Thr Ser Leu Ser Asp Ile Thr Ser Met Ala Glu Gly Glu Leu Ala
465                 470                 475                 480

Ala Lys Leu Thr Ser Phe Met Phe Gly His Val
                485                 490
```